United States Patent
Dede et al.

(10) Patent No.: US 6,765,036 B2
(45) Date of Patent: Jul. 20, 2004

(54) TERNARY PHOTOINITIATOR SYSTEM FOR CATIONICALLY POLYMERIZABLE RESINS

(75) Inventors: Karsten Dede, Landsberg (DE);
Thomas Klettke, Schondorf (DE);
Thomas Luchterhandt, Krailling (DE);
Joel D. Oxman, Minneapolis, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 104 days.

(21) Appl. No.: 10/050,218

(22) Filed: Jan. 15, 2002

(65) Prior Publication Data

US 2003/0166737 A1 Sep. 4, 2003

(51) Int. Cl.$^7$ ................ C08F 2/46; C08F 2/50
(52) U.S. Cl. .......... 522/15; 522/100; 522/14; 522/25; 522/26; 522/28; 522/29; 522/31; 522/81; 522/83; 522/170; 522/908; 523/116; 433/228.1; 206/63.5; 106/35
(58) Field of Search .............. 522/15, 14, 26, 522/25, 28, 29, 31, 81, 83, 100, 170, 908; 523/116; 433/228.1; 206/63.5; 106/35

(56) References Cited

U.S. PATENT DOCUMENTS

| | | | |
|---|---|---|---|
| 3,729,313 A | 4/1973 | Smith | |
| 3,741,769 A | 6/1973 | Smith | |
| 3,808,006 A | 4/1974 | Smith | |
| 4,250,053 A | 2/1981 | Smith | |
| 4,256,828 A | 3/1981 | Smith | |
| 4,394,403 A | 7/1983 | Smith | |
| 4,503,169 A | 3/1985 | Randklev | |
| 4,629,746 A | 12/1986 | Michl et al. | |
| 4,642,126 A | 2/1987 | Zador et al. | |
| 4,652,274 A | 3/1987 | Boettcher et al. | |
| 4,695,251 A | 9/1987 | Randklev | |
| 4,735,632 A * | 4/1988 | Oxman et al. ........ | 51/295 |
| 4,767,798 A | 8/1988 | Gasser et al. | |
| 4,828,583 A * | 5/1989 | Oxman et al. ........ | 51/295 |
| 4,835,193 A | 5/1989 | Hayase et al. | |
| 4,882,365 A | 11/1989 | Gasser et al. | |
| 4,889,792 A * | 12/1989 | Palazzotto ........... | 430/281.1 |
| 4,959,297 A * | 9/1990 | Palazzotto ........... | 430/322 |
| 5,545,676 A | 8/1996 | Palazzotto et al. | |
| 5,730,764 A * | 3/1998 | Williamson et al. .... | 51/295 |
| 5,856,373 A | 1/1999 | Kaisaki et al. | |
| 5,980,253 A * | 11/1999 | Oxman et al. ........ | 433/228.1 |
| 5,998,495 A | 12/1999 | Oxman et al. | |
| 6,025,406 A | 2/2000 | Oxman et al. | |
| 6,043,295 A | 3/2000 | Oxman et al. | |
| 6,084,004 A | 7/2000 | Weinmann et al. | |
| 6,085,004 A * | 7/2000 | Dower et al. ........ | 385/80 |
| 6,151,433 A * | 11/2000 | Dower et al. ........ | 385/86 |
| 6,187,833 B1 | 2/2001 | Oxman et al. | |
| 6,187,836 B1 * | 2/2001 | Oxman et al. ........ | 522/148 |
| 6,306,926 B1 | 10/2001 | Bretscher et al. | |
| 6,331,080 B1 * | 12/2001 | Cole et al. .......... | 385/80 |

FOREIGN PATENT DOCUMENTS

| | | | |
|---|---|---|---|
| EP | 285369 A2 * | 10/1988 | ........ B24D/3/28 |
| EP | 0 728 970 A2 | 8/1996 | |
| WO | WO 95/14716 A1 | 6/1995 | |
| WO | WO 98/22521 A1 | 5/1998 | |
| WO | WO 98/47046 A1 | 10/1998 | |
| WO | WO 98/47047 A1 | 10/1998 | |
| WO | WO 99/27892 A2 | 6/1999 | |
| WO | WO 00/19966 A1 | 4/2000 | |
| WO | WO 00/19967 A1 | 4/2000 | |

OTHER PUBLICATIONS

Beringer et al., "Diaryliodonium Salts. IX. The Synthesis of Substituted Diphenyliodonium Slats," *J. Am. Chem. Soc.* vol. 81, pp. 342–351 (1959).
N.L. Weinburg, Ed., "Technique of Electroorganic Synthesis," *Techniques of Chemistry*, vol. V, Part. II (1975).
C.K. Mann and K.K. Barnes, *Electrochemical Reactions in Nonaqueous Systems* (1970).

* cited by examiner

*Primary Examiner*—James J. Seidleck
*Assistant Examiner*—Sanza L. McClendon
(74) *Attorney, Agent, or Firm*—Sean J. Edman

(57) ABSTRACT

Photopolymerizable compositions comprise a cationically polymerizable resin and a photoinitiator system comprising: (i) an iodonium salt; (ii) a visible light sensitizer; and (iii) an electron donor compound having an oxidation potential less than that of 1,4-dimethoxybenzene when measured versus a saturated calomel electrode, wherein the photoinitiator system has a photoinduced potential of less than that of 3-dimethylaminobenzoic acid in a standard solution of $2.9 \times 10^{-5}$ moles/g diphenyl iodonium hexafluoroantimonate and $1.5 \times 10^{-5}$ moles/g camphorquinone in 2-butanone. The compositions polymerize on exposure to light in the visible spectrum and are useful in a variety of applications, including dental adhesives and dental composites.

44 Claims, No Drawings

TERNARY PHOTOINITIATOR SYSTEM FOR CATIONICALLY POLYMERIZABLE RESINS

FIELD OF THE INVENTION

In general, this invention relates to a ternary photoinitiator system for cationically polymerizable resins. More specifically, this invention relates to photopolymerizable compositions that contain a cationically polymerizable resin and a ternary photoinitiator system that is activated upon exposure to actinic radiation. This invention also relates to methods of polymerizing such compositions using this photoinitiator system.

BACKGROUND OF THE INVENTION

Epoxy-containing compounds are known to be curable using various cationic initiator systems. Smith, U.S. Pat. No. 4,256,828, describes photopolymerizable compositions that contain epoxides, an organic compound with hydroxyl functionality, and a photosensitive aromatic sulfonium or iodonium salt of a halogen containing complex ion. Hayase et al., U.S. Pat. No. 4,835,193, describe photopolymerizable epoxy resin compositions that comprise an epoxy resin and a heteropoly-acid aromatic sulfonium salt as the photocuring catalyst. In WO 95/14716 Neckers et al. describe photohardenable compositions that comprise a cationically polymerizable compound, a xanthene or fluorone dye, a hydrogen donor, and an onium salt. Palazzotto et al., U.S. Pat. No. 5,545,676, describe addition polymerization of free-radically polymerizable materials. The disclosed photoinitiator system comprises an aryliodonium salt, a sensitizer, and an electron donor having an oxidation potential less than or equal to that of p-dimethoxybenzene.

Oxman et al., U.S. Pat. Nos. 6,025,406 and 6,043,295, describe a ternary photoinitiator system for curing of epoxy resins. Oxman et al., U.S. Pat. Nos. 5,998,495 and 6,187,833, describe a ternary photoinitiator system for curing of epoxy/polyol resins. For both the epoxy resins and the epoxy/polyol resins, the ternary photoinitiator system comprises an iodonium salt, a visible light sensitizer, and an electron donor, wherein the photoinitiator system has a photoinduced potential greater than or equal to that of 3-dimethylaminobenzoic acid in a standard solution of $2.9 \times 10^{-5}$ moles/g diphenyl iodonium hexafluoroantimonate and $1.5 \times 10^{-5}$ moles/g camphorquinone in 2-butanone.

Weinmann et al., U.S. Pat. No. 6,084,004, describe compositions that undergo cationic curing and comprise a diaryliodonium compound, an alpha-dicarbonyl compound, a compound containing epoxide and/or oxetane groups, and an aromatic amine.

SUMMARY OF THE INVENTION

Briefly, and in one aspect, the invention provides a photoinitiator system for a cationically polymerizable resin. The photoinitiator system comprises an iodonium salt, a visible light sensitizer, and an electron donor compound having an oxidation potential greater than 0 and less than that of 1,4-dimethoxybenzene when measured versus a saturated calomel electrode. The photoinitiator system has a photoinduced potential less than that of 3-dimethylaminobenzoic acid in a standard solution of $2.9 \times 10^{-5}$ moles/g diphenyl iodonium hexafluoroantimonate and $1.5 \times 10^{-5}$ moles/g camphorquinone in 2-butanone.

In another aspect the invention provides a photopolymerizable composition comprising a cationically polymerizable resin, and a photoinitiator system like that described above. Optionally, the photopolymerizable composition may further comprise a free-radically polymerizable resin and/or a hydroxyl-containing material.

The cationically polymerizable resin may be selected from epoxy, oxetane, vinyl ether and spiro-orthocarbonate resins, and combinations thereof. Preferably, the cationically polymerizable resin comprises an epoxy resin, especially a silicon-containing epoxy resin, or a blend of a silicon-containing epoxy resin and an epoxy resin that does not contain silicon.

The iodonium salt may be a diaryl iodonium salt such as diaryliodonium hexafluorophosphate, diaryliodonium hexafluoroantimonate, 4-octyloxyphenyl phenyliodonium hexafluoroantimonate, 4-(2-hydroxytetradylecoxyphenyl) phenyliodonium hexafluoroantimonate, 4-(1-methylethyl) phenyl 4-methylphenyliodonium tetrakis (pentafluorophenyl)borate, and combinations thereof.

The visible light sensitizer may be selected from ketones, coumarin dyes, xanthene dyes, fluorone dyes, fluorescein dyesaminoketone dyes, p-substituted aminostyryl ketone compounds, and combinations thereof. More preferably, the visible light sensitizer is an alpha-diketone; camphorquinone is particularly preferred.

Preferred electron donor compounds for use in the invention possess one or more (and more preferably several if not all) of the following properties: (a) they are soluble in the polymerizable composition; (b) they do not absorb a significant amount of light at the wavelength of the light used to photopolymerize the composition, typically the wavelength at which the visible light sensitizer exhibits maximum absorption, by which it is meant that the electron donor compound does not detrimentally affect the performance of the visible light sensitizer; (c) they have an oxidation potential ($E_{ox}$) greater than 0 but less than that of 1,4-dimethoxybenzene when measured versus a saturated calomel electrode (more preferably an oxidation potential less than about 1.35 volts, and most preferably an oxidation potential between about 0.5 and 1.34 volts); (d) they yield a photoinitiator system that has a photoinduced potential less than that of 3-dimethylaminobenzoic acid in a standard solution of $2.9 \times 10^{-5}$ moles/g diphenyl iodonium hexafluoroantimonate and $1.5 \times 10^{-5}$ moles/g camphorquinone in 2-butanone; (e) a $pk_b$ greater than 8; (f) they impart not more than a minimal amount of objectionable color to the polymerized resin; (g) they impart not more than a minimal amount of objectionable fluorescence to the polymerized resin; (h) they cause no more than a minimal amount of polymerization inhibition; (i) they improve the shelf life stability of the photopolymerizable composition; (j) they can be used in a lower effective concentration than other polymerization aids; and (k) they can increase the polymerization speed of a polymerizable composition relative to the same composition but not containing the electron donor compound (e.g., a polymerizable composition containing such an electron donor compound can cure after less than about 2 minutes exposure to a light source that generates light of a wavelength to which the visible light sensitizer is sensitive).

Preferred electron donor compounds are polycylic aromatic compounds (such as biphenylenes, naphthalenes, anthracenes, benzanthracenes, pyrenes, azulenes, pentacenes, decacyclenes, and derivatives (e.g., acenaphthenes) and combinations thereof), and N-alkyl carbazole compounds (e.g., N-methyl carbazole).

Photopolymerizable compositions according to the invention can provide a wide variety of utilities such as a photopolymerizable adhesive, a curable ink imaging layer, a silverless imaging layer, an imaging layer on a projection plate, an imaging layer on a laser plate, a hard coat layer on an optical lens, or a coating on an optical fiber. The photopolymerizable compositions of the invention are especially useful as dental materials such as dental adhesives and dental composites.

In another aspect, the invention provides a method for reducing the time needed to polymerize a cationically polymerizable resin. The method comprises the steps of:

a) providing a cationically polymerizable resin;

b) providing a photoinitiator system like that described above for the cationically polymerizable resin;

c) combining the cationically polymerizable resin and the photoinitiator system to provide a polymerizable mixture; and d) exposing the polymerizable mixture to a light source having a wavelength and intensity to which the photoinitiator system is reactive and for a time until the polymerizable mixture attains a hard, tack-free state;

wherein the time until the polymerizable mixture attains a hard, tack-free state is less than the time required for the same polymerizable mixture, but excluding the electron donor compound, to achieve the same hard, tack-free state when exposed to the same light source.

DETAILED DESCRIPTION OF THE PREFERRED EMBODIMENTS

Broadly, and in one aspect, this invention provides a photopolymerizable composition that comprises a cationically polymerizable resin, and a photoinitiator system that contains an iodonium salt, a visible light sensitizer, and an electron donor compound, wherein the electron donor compound has an oxidation potential greater than 0 but less than that of 1,4-dimethoxybenzene when measured versus a saturated calomel electrode (SCE), and further wherein the photoinitiator system has a photoinduced potential less than that of 3-dimethylaminobenzoic acid in a standard solution of $2.9 \times 10^{-5}$ moles/g diphenyl iodonium hexafluoroantimonate and $1.5 \times 10^{-5}$ moles/g camphorquinone in 2-butanone.

Advantageously, the photopolymerizable compositions of the invention are sensitive throughout the "visible light" region and polymerize without appreciable application of heat. The term "visible light" is used throughout this application to refer to light having a wavelength of about 400 to 1000 nanometers (nm). Photopolymerization of the compositions takes place upon exposure of the compositions to a source of actinic radiation having a wavelength within this spectral region.

The cationically polymerizable resins useful in the compositions of the invention include, for example, epoxy (including silicon-containing epoxy), oxetane, spiro-orthocarbonate, and, vinyl ether resins, as well as combinations thereof.

Useful epoxy resins are organic compounds having an oxirane ring, i.e., a group of the formula

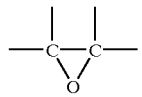

which is polymerizable by ring opening. Such materials, broadly called epoxides, include monomeric epoxy compounds and epoxides of the polymeric type and can be aliphatic, cycloaliphatic, aromatic or heterocyclic. These materials generally have, on the average, at least 1 polymerizable epoxy group per molecule, preferably at least about 1.5, and more preferably at least about 2 polymerizable epoxy groups per molecule. The polymeric epoxides include linear polymers having terminal epoxy groups (e.g., a diglycidyl ether of a polyoxyalkylene glycol), polymers having skeletal oxirane units (e.g., polybutadiene polyepoxide), and polymers having pendent epoxy groups (e.g., a glycidyl methacrylate polymer or copolymer). The epoxides may be pure compounds or may be mixtures of compounds containing one, two, or more epoxy groups per molecule. The "average" number of epoxy groups per molecule is determined by dividing the total number of epoxy groups in the epoxy resin by the total number of epoxy-containing molecules present.

These epoxy resins may vary from low molecular weight monomeric materials to high molecular weight polymers and may vary greatly in the nature of their backbone and substituent groups. For example, the backbone may be of any type and substituent groups thereon can be any group that does not substantially interfere with cationic polymerization at room temperature. Illustrative of permissible substituent groups are halogens, ester groups, ethers, sulfonate groups, siloxane groups, nitro groups, phosphate groups, and the like. The molecular weight of the epoxy resin may vary from about 58 to about 100,000 or more.

Particularly preferred epoxy resins include those which contain cyclohexene oxide groups such as epoxycyclohexanecarboxylates, typified by 3,4-epoxycyclohexylmethyl-3,4-epoxycyclohexanecarboxylate, 3,4-epoxy-2-methylcyclohexylmethyl-3,4-epoxy-2-methylcyclohexane carboxylate, and bis(3,4-epoxy-6-methylcyclohexylmethyl)adipate. For a more detailed list of useful epoxides of this nature, reference is made to U.S. Pat. Nos. 3,117,099 and 6,245,828, International Patent Publication No. WO 01/51540, European Patent Publication No. 0 412 430, and Japanese Patent Publication No. 51-033541. Other epoxy resins that are useful in the compositions of this invention include glycidyl ether monomers of the formula

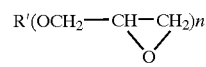

where R' is alkyl or aryl, and n is an integer of 1 to 6. Examples are glycidyl ethers of polyhydric phenols obtained by reacting a polyhydric phenol with an excess of chlorohydrin such as epichlorohydrin (e.g., the diglycidyl ether of 2,2-bis-(2,3-epoxypropoxyphenol)propane). Further examples of epoxides of this type are described in U.S. Pat. No. 3,018,262, and in "Handbook of Epoxy Resins" by Lee and Neville, McGraw-Hill Book Co., New York (1967).

There is a host of commercially available epoxy resins that can be used in this invention. In particular, epoxides that are readily available include octadecylene oxide, epichlorohydrin, styrene oxide, vinyl cyclohexene oxide, glycidol, glycidylmethacrylate, diglycidyl ether of Bisphenol A (e.g., those available under the trade designations "Epon 828", "Epon 825", "Epon 1004" and "Epon 1010" from Shell Chemical Co., "DER-331", "DER-332", and "DER-334", from Dow Chemical Co.), vinylcyclohexene dioxide (e.g., "ERL-4206" from Union Carbide Corp.), 3,4-epoxycyclohexylmethyl-3,4-epoxycyclohexene carboxylate (e.g., "ERL-4221" or "CYRACURE UVR 6110" or UVR 6105" from Union Carbide Corp.), 3,4-epoxy-6-methylcyclohexylmethyl-3,4-epoxy-6-methyl-cyclohexene carboxylate (e.g., "ERL-4201" from Union Carbide Corp.), bis(3,4-epoxy-6-methylcyclohexylmethyl)adipate (e.g., "ERL-4289" from Union Carbide Corp.), bis(2,3-epoxycyclopentyl) ether (e.g., "ERL-0400" from Union Carbide Corp.), aliphatic epoxy modified from polypropylene glycol (e.g., "ERL-4050" and "ERL-4052" from Union Carbide Corp.), dipentene dioxide (e.g., "ERL-4269" from Union Carbide Corp.), epoxidized polybutadiene (e.g., "Oxiron 2001" from FMC Corp.), silicone resin containing epoxy functionality, flame retardant epoxy resins (e.g., "DER-580", a brominated bisphenol type epoxy resin available from Dow Chemical Co.), 1,4-butanediol diglycidyl ether of phenolformaldehyde novolak (e.g., "DEN-431" and "DEN-438" from Dow Chemical Co.), and resorcinol diglycidyl ether (e.g., "Kopoxite" from Koppers Company, Inc.), bis(3,4-epoxycyclohexyl)adipate (e.g., "ERL-4299" or "UVR-6128", from Union Carbide Corp.), 2-(3,4-epoxycyclohexyl-5,5-spiro-3,4-epoxy)cyclohexane-meta-dioxane (e.g., "ERL-4234" from Union Carbide Corp.), vinylcyclohexene monoxide 1,2-epoxyhexadecane (e.g., "UVR-6216" from Union Carbide Corp.), alkyl glycidyl ethers such as alkyl $C_8$–$C_{10}$ glycidyl ether (e.g., "HELOXY Modifier 7" from Shell Chemical Co.), alkyl $C_{12}$–$C_{14}$ glycidyl ether (e.g., "HELOXY Modifier 8" from Shell Chemical Co.), butyl glycidyl ether (e.g., "HELOXY Modifier 61" from Shell Chemical Co.), cresyl glycidyl ether (e.g., "HELOXY Modifier 62" from Shell Chemical Co.), p-tert-butylphenyl glycidyl ether (e.g., "HELOXY Modifier 65" from Shell Chemical Co.), polyfunctional glycidyl ethers such as diglycidyl ether of 1,4-butanediol (e.g., "HELOXY Modifier 67" from Shell Chemical Co.), diglycidyl ether of neopentyl glycol (e.g., "HELOXY Modifier 68" from Shell Chemical Co.), diglycidyl ether of cyclohexanedimethanol (e.g., "HELOXY Modifier 107" from Shell Chemical Co.), trimethylol ethane triglycidyl ether (e.g., "HELOXY Modifier 44" from Shell Chemical Co.), trimethylol propane triglycidyl ether (e.g., "HELOXY Modifier 48" from Shell Chemical Co.), polyglycidyl ether of an aliphatic polyol (e.g., "HELOXY Modifier 84" from Shell Chemical Co.), polyglycol diepoxide (e.g., "HELOXY Modifier 32" from Shell Chemical Co.), bisphenol F epoxides (e.g., "EPN-1138" or "GY-281" from Ciba-Geigy Corp.), 9,9-bis[4-(2,3-epoxypropoxy)-phenyl]fluorenone (e.g., "Epon 1079" from Shell Chemical Co.).

Still other useful epoxy resins contain copolymers of acrylic acid esters or glycidol such as glycidylacrylate and glycidylmethacrylate with one or more copolymerizable vinyl compounds. Examples of such copolymers are 1:1 styrene-glycidylmethacrylate, 1:1 methylmethacrylate-glycidylacrylate and a 62.5:24:13.5 methylmethacrylate-ethyl acrylate-glycidylmethacrylate.

Other useful epoxy resins include epichlorohydrins, alkylene oxides, e.g., propylene oxide, styrene oxide; alkenyl oxides, e.g., butadiene oxide; and glycidyl esters, e.g., ethyl glycidate.

Particulary preferred epoxies are those that contain silicon, useful examples of which are described in International Patent Publication No. WO 01/51540, such as: 7-Oxabicyclo[4.1.0]heptane; 3,3',3'',3'''-[(2,4,6,8-tetramethylcyclotetrasiloxan-2,4,6,8-tetrayl)tetra-2,1-ethandiyl]tetrakis-; 7-Oxabicyclo[4.1.0]heptan, 3,3',3'',3''', 3''''-[(2,4,6,8,10-pentamethylcyclopentasiloxan-2,4,6,8,10-pentayl)penta-2,1-ethandiyl]pentakis-, Silane; methylbis[2-(7-oxabicyclo[4.1.0]hept-3-yl)ethyl]phenyl-; Silane, dimethylbis[2-(7-oxabicyclo[4.1.0]hept-3-yl)methyl]-; Silane, dimethyl[2-(7-oxabicyclo[4.1.0]hept-3-yl)methyl] [2-(7-oxabicyclo[4.1.0]hept-3-yl)ethyl]-; Silane, 1,4-phenylenbis[dimethyl[2-(7-oxabicyclo[4.1.0]hept-3-yl) ethyl]]-; Silane 1,2-ethylenbis[dimethyl[2-(7-oxabicyclo [4.1.0]hept-3-yl)ethyl]]-; Silane;dimethylbis [2-(7-oxabicyclo[4.1.0]hept-3-yl)ethyl]-; 1,3-Bis[2-(3,4-epoxycyclohexyl)ethyl]-1,1,3,3-tetramethyldisiloxane; Silane 2,5-bicyclo[2.2.1.]heptylenbis[dimethyl[2-(7-oxabicyclo[4.1.0]hept-3-yl)ethyl]]-; Silane 1,6-hexylenbis [dimethyl[2-(7-oxabicyclo[4.1.0]hept-3-yl)ethyl]]-; Silane 1,1',1''-(1,2,4-cyclohexylentris(dimethyl[2-(7-oxabicyclo [4.1.0]hept-3-yl)ethyl]))-; Trisiloxane, 3-[[dimethyl[2-(7-oxabicyclo[4.1.0]hept-3-yl)ethyl]silyl]oxy]-1,1,5,5-tetramethyl-1,5-bis[2-(7-oxabicyclo[4.1.0]hept-3-yl)ethyl]-3-phenyl-; Disiloxane 1,1',1''-(1,2,4-cyclohexanetriyltri-2,1-ethanediyl)tris[1,1,3,3-tetramethyl-3-[2-(7-oxabicyclo [4.1.0]hept-3-yl)ethyl]]-; Trisiloxane, 3,3-bis[[dimethyl[2-(7-oxabicyclo[4.1.0]hept-3-yl)ethyl]silyl]oxy]-1,1,5,5-tetramethyl-1,5-bis[2-(7-oxabicyclo[4.1.0]hept-3-yl) ethyl]-; Trisiloxane, 3-[[dimethyl[2-(7-oxabicyclo[4.1.0] hept-3-yl)ethyl]silyl]oxy]-1,1,3,5,5-pentamethyl-1,5-bis[2-(7-oxabicyclo[4.1.0]hept-3-yl)ethyl],-1,3,5,7-tetrakis(2,1-ethandiyl-3,4-epoxycyclohexyl)-1,3,5,7-tetramethylcyclotetrasiloxane and 1,3,5,7,9-pentakis(2,1-ethandiyl-3,4-epoxycyclohexyl)-1,3,5,7,9-pentamethylcyclopentasiloxane.

The cationically polymerizable resin may also be provided by a vinyl ether resin. Examples of vinyl ether resins that may be used include, but are not limited to, tri(ethylene glycol) divinyl ether (TEGDVE), glycidyl vinyl ether (GVE), butanediolvinyl ether (BDVE), di(ethylene glycol) divinyl ether (DEGDVE), 1,4-cyclohexanedimethdiol divinyl ether(CHDMDVE), 4-(isopropenyloxymethyl)-1,3-dioxolan-2-one (POMDO), 2-chloroethyl vinyl ether (CEVE), 2-ethylhexyl vinyl ether (EHVE), ethyl vinyl ether (EVE), n-propyl vinyl ether (NPVE), isopropyl vinyl ether (IPVE), n-butyl vinyl ether (NBVE), isobutyl vinyl ether (IBVE), octadecyl vinyl ether (ODVE), cyclohexyl vinyl ether (CVE), butanediol divinyl ether (BDDVE), hydroxybutyl vinyl ether (HBVE), cyclohexanedimethanol monovinyl ether (CHMVE), tert-butyl vinyl ether (TBVE), tert-amyl vinyl ether (TAVE), dodecyl vinyl ether (DDVE), ethylene glycol divinyl ether (EGDVE), ethylene glycol monovinyl ether (EGMVE), hexanediol divinyl ether (HDDVE), hexanediol monovinyl ether (HDMVE), diethylene glycol monovinyl ether (MVE-2), triethyleneglycol methyl vinyl ether (MTGVE), tetraethylene glycol divinyl ether (DVE-4), trimethylolpropane trivinyl ether (TMPTVE), aminopropyl vinyl ether (APVE), polytetrahydrofuran divinyl ether (PTHFDVE), n-butyl vinyl ether (n-BVE), 4-hydroxybutyl vinyl ether (HBVE), ethylene glycol butyl vinyl ether (EGBVE), 2-diethylamino ethyl vinyl ether (DEAEVE), dipropylene glycol divinyl ether (DPGDVE), a vinyl ether terminated aromatic ester monomer (e.g., hydroxybutyl vinyl ether isophthalate which can be purchased from Allied-Signal Inc., Engineered Materials Sector, Morristown, N.J. under the trademark VECTOMER 4010), a vinyl ether terminated aliphatic ester monomer (e.g., cyclohexane dimethanol monovinyl ether glutarate which can be purchased from Allied-Signal Inc. under the trademark VECTOMER 4020), a vinyl ether terminated aliphatic urethane oligomer (e.g., VECTOMER 2020 which can be purchased from Allied-Signal Inc.), and a vinyl ether terminated aromatic urethane oligomer (e.g., VECTOMER 2015 and VECTOMER 2010, both of which can be purchased from Allied-Signal Inc.

Blends of various cationically polymerizable resins are also contemplated in this invention. Examples of such blends include two or more weight average molecular weight distributions of resin-containing compounds, such as low molecular weight (below 200), intermediate molecular weight (about 200 to 10,000) and higher molecular weight (above about 10,000). Alternatively or additionally, the resin may contain a blend of resin-containing materials having different chemical natures, such as aliphatic and aromatic, or functionalities, such as polar and non-polar. Other cationically polymerizable polymers may additionally be incorporated, if desired.

The optional hydroxyl-containing material that may be used in the present invention can be any organic material having hydroxyl functionality of at least 1, and preferably at least 2.

Preferably the hydroxyl-containing material contains two or more primary or secondary aliphatic hydroxyl groups (i.e., the hydroxyl group is bonded directly to a non-aromatic carbon atom). The hydroxyl groups can be terminally situated, or they can be pendent from a polymer or copolymer. The molecular weight of the hydroxyl-containing organic material can vary from very low (e.g., 32) to very high (e.g., one million or more). Suitable hydroxyl-containing materials can have low molecular weights, i.e. from about 32 to 200, intermediate molecular weight, i.e. from about 200 to 10,000, or high molecular weight, i.e. above about 10,000. As used herein, all molecular weights are weight average molecular weights.

The hydroxyl-containing material can optionally contain other functionalities that do not substantially interfere with cationic polymerization at room temperature. Thus, the hydroxyl-containing materials can be nonaromatic in nature or can contain aromatic functionality. The hydroxyl-containing material can optionally contain heteroatoms in the backbone of the molecule, such as nitrogen, oxygen, sulfur, and the like, provided that the ultimate hydroxyl-containing material does not substantially interfere with cationic polymerization at room temperature. The hydroxyl-containing material can, for example, be selected from naturally occurring or synthetically prepared cellulosic materials. Of course, the hydroxyl-containing material is also substantially free of groups that may be thermally or photolytically unstable; that is, the material will not decompose or liberate volatile components at temperatures below about 100° C. or in the presence of actinic light that may be encountered during the desired polymerization conditions for the photocopolymerizable composition.

Representative examples of suitable hydroxyl-containing materials having a hydroxyl functionality of 1 include alkanols, monoalkyl ethers of polyoxyalkyleneglycols, monoalkyl ethers of alkylene-glycols, and others known in the art.

Representative examples of useful monomeric polyhydroxy organic materials include alkylene glycols (e.g., 1,2-ethanediol; 1,3-propanediol; 1,4-butanediol; 1,6-hexanediol; 1,8-octanediol; 2-ethyl-1,6-hexanediol; bis(hydroxymethyl)cyclohexane; 1,18-dihydroxyoctadecane; 3-chloro-1,2-propanediol); polyhydroxyalkanes (e.g., glycerine, tri-methylolethane, pentaerythritol, sorbitol) and other polyhydroxy compounds such as N,N-bis(hydroxyethyl)benzamide; 2-butyne-1,4-diol; 4,4-bis(hydroxymethyl)diphenylsulfone; castor oil; and the like.

Representative examples of useful polymeric hydroxyl-containing materials include polyoxyethylene and polyoxypropylene glycols, and particularly the polyoxyethylene and polyoxypropylene glycol diols and triols having molecular weights from about 200 to about 10,000 corresponding to a hydroxy equivalent weight of 100 to 5000 for the diols or 70 to 3300 for triols; polytetramethylene ether glycols such as polytetrahydrofuran or "poly THF" of varying molecular weight; copolymers of hydroxypropyl and hydroxyethyl acrylates and methacrylates with other free radical-polymerizable monomers such as acrylate esters, vinyl halides, or styrene; copolymers containing pendent hydroxy groups formed by hydrolysis or partial hydrolysis of vinyl acetate copolymers, polyvinylacetal resins containing pendent hydroxyl groups; modified cellulose polymers such as hydroxyethylated and hydroxypropylated cellulose; hydroxy-terminated polyesters; hydroxy-terminated polylactones, and particularly the polycaprolactones; fluorinated polyoxyethylene or polyoxypropylene glycols; and hydroxy-terminated polyalkadienes.

Useful commercially available hydroxyl-containing materials include the "TERATHANE" series of polytetramethylene ether glycols such as "TERATHANE" 650, 1000, 2000 and 2900 (available from du Pont de Nemours, Wilmington, Del.), polytetrahydrofuran with an average molecular weight of 250 (available from Sigma-Aldrich, St. Louis, Mo.), the "PEP" series of polyoxyalkylene tetrols having secondary hydroxyl groups such as "PEP" 450, 550 and 650; "BUTVAR" series of polyvinylacetal resins such as "BUTVAR" B-72A, B-73, B-76, B-90 and B-98 (available from Monsanto Chemical Company, St. Louis, Mo.); and the "FORMVAR" series of resins such as 7/70, 12/85, 7/95S, 7/95E, 15/95S and 15/95E (available from Monsanto Chemical Company); the "TONE" series of polycaprolactone polyols such as "TONE" 0200, 0210, 0230, 0240, 0300 and 0301 (available from Union Carbide); "PARAPLEX U-148" aliphatic polyester diol (available from Rohm and Haas, Philadelphia, Pa.), the "MULTRON" R series of saturated polyester polyols such as "MULTRON" R-2, R-12A, R-16, R-18, R-38, R-68 and R-74 (available from Mobay Chemical Co.); "KLUCEL E" hydroxypropylated cellulose having an equivalent weight of approximately 100 (available from Hercules Inc.); "Alcohol Soluble Butyrate" cellulose acetate butyrate ester having a hydroxyl equivalent weight of approximately 400 (available from Eastman Kodak Co., Rochester, N.Y.); polyether polyols such as polypropylene glycol diol (e.g., "ARCOL PPG-425", "Arcol PPG-725", "ARCOL PPG-1025", "ARCOL PPG-2025", ARCOL PPG-3025", "ARCOL PPG-4025" from ARCO Chemical Co.); polypropylene glycol triol (e.g., "ARCOL LT-28", "ARCOL LHT-42", "ARCOL LHT 112", "ARCOL LHT 240", "ARCOL LG-56", "ARCOL LG-168", "ARCOL LG-650" from ARCO Chemical Co.); ethylene oxide capped polyoxypropylene triol or diol (e.g., "ARCOL 11-27", "ARCOL 11-34", "ARCOL E-351", "ARCOL E-452", "ARCOL E-785", "ARCOL E-786" from ARCO Chemical Co.); ethoxylated bis-phenol A; propylene oxide or ethylene oxide-based polyols (e.g., "VORANOL" polyether polyols from the Dow Chemical Co.).

The amount of hydroxyl-containing organic material optionally used in the compositions of the invention may vary over broad ranges, depending upon factors such as the compatibility of the hydroxyl-containing material with the resin, the equivalent weight and functionality of the hydroxyl-containing material, the physical properties desired in the final cured composition, the desired speed of photopolymerization, and the like.

Blends of various hydroxyl-containing materials are also contemplated in this invention. Examples of such blends include two or more molecular weight distributions of hydroxyl-containing compounds, such as low molecular weight (below 200), intermediate molecular weight (about 200 to 10,000) and higher molecular weight (above about 10,000). Alternatively or additionally, the hydroxyl-containing material can contain a blend of hydroxyl-containing materials having different chemical natures, such as aliphatic and aromatic, or functionalities, such as polar and non-polar. As an additional example, one may use mixtures of two or more poly-functional hydroxy materials or one or more mono-functional hydroxy materials with poly-functional hydroxy materials.

If desired, the photopolymerizable composition can also contain a free-radically polymerizable material, including ethylenically unsaturated monomer, monomers or oligomers or polymers. Suitable materials contain at least one ethylenically unsaturated bond, and are capable of undergoing addition polymerization. Such free-radically polymerizable materials include mono-, di- or poly-acrylates and methacrylates such as methyl acrylate, methyl methacrylate, ethyl acrylate, isopropyl methacrylate, n-hexyl acrylate, stearyl acrylate, allyl acrylate, glycerol diacrylate, glycerol triacrylate, ethyleneglycol diacrylate, diethyleneglycol diacrylate, triethyleneglycol dimethacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexacrylate, bis[1-(2-acryloxy)]-p-ethoxyphenyldimethylmethane, bis[1-(3-acryloxy-2-hydroxy)]-p-propoxyphenyldimethylmethane, and trishydroxyethyl-isocyanurate trimethacrylate; the bis-acrylates and bis-methacrylates of polyethylene glycols of molecular weight 200–500, copolymerizable mixtures of acrylated monomers such as those in U.S. Pat. No. 4,652,274, and acrylated oligomers such as those of U.S. Pat. No. 4,642,126; and vinyl compounds such as styrene, diallyl phthalate, divinyl succinate, divinyl adipate and divinylphthalate. Mixtures of two or more of these free radically polymerizable materials can be used if desired.

If desired, the polymerizable material(s) may contain both cationically polymerizable and free-radically polymerizable functionalities in a single molecule. These may be obtained, for example, by reacting a di- or poly-epoxide with one or more equivalents of an ethylenically unsaturated carboxylic acid. Examples of such materials include the reaction product of UVR-6105 (available from Union Carbide) or DER 332 (available from Dow Chemical Co.) with one equivalent of methacrylic acid. Commercially available materials having epoxy and free-radically polymerizable functionalities include the "Cyclomer" series, such as Cyclomer M100 or M101, available from Daicel Chemical, Japan.

The polymerizable material(s) can also contain hydroxyl and free-radically polymerizable functionalities in a single molecule. Examples of such materials include hydroxyalkylacrylates and hydroxyalkylmethacrylates such as hydroxyethylacrylate, hydroxyethylmethacrylate; glycerol mono- or di-acrylate and methacrylate; and the like.

The cationically polymerizable resin, optional hydroxy-containing material(s), and optional free radically polymerizable material(s) are combined with a three-component or ternary photoinitiator system. The first component in the photoinitiator system is an iodonium salt, e.g., a diaryliodonium salt. The iodonium salt should be soluble in the composition and preferably is shelf-stable, meaning it does not spontaneously promote polymerization when dissolved therein in the presence of the visible light sensitizer and the electron donor compound. Accordingly, selection of a particular iodonium salt may depend to some extent upon the particular resin, visible light sensitizer and electron donor that are chosen. Suitable iodonium salts are described in U.S. Pat. Nos. 3,729,313, 3,741,769, 3,808,006, 4,250,053 and 4,394,403. The iodonium salt can be a simple salt, containing an anion such as $Cl^-$, $Br^-$, $I^-$ or $C_2H_5SO_3^-$; or a metal complex salt containing an antimonate, arsenate, phosphate or borate such as $SbF_5OH^-$ or $AsF_6^-$. Mixtures of iodonium salts can be used if desired.

Examples of useful aromatic iodonium complex salt photoinitiators include: diphenyliodonium tetrafluoroborate; di(4-methylphenyl)iodonium tetrafluoroborate; phenyl-4-methylphenyliodonium tetrafluoroborate; di(4-heptylphenyl)iodonium tetrafluoroborate; di(3-nitrophenyl) iodonium hexafluorophosphate; di(4-chlorophenyl) iodonium hexafluorophosphate; di(naphthyl)iodonium tetrafluoroborate; di(4-trifluoromethylphenyl)iodonium tetrafluoroborate; diphenyliodonium hexafluorophosphate; di(4-methylphenyl)iodonium hexafluorophosphate; diphenyliodonium hexafluoroarsenate; di(4-phenoxyphenyl) iodonium tetrafluoroborate; phenyl-2-thienyliodonium hexafluorophosphate; 3,5-dimethylpyrazolyl-4-phenyliodonium hexafluorophosphate; diphenyliodonium hexafluoroantimonate; 2,2'-diphenyliodonium tetrafluoroborate; di(2,4-dichlorophenyl)iodonium hexafluorophosphate; di(4-bromophenyl)iodonium hexafluorophosphate; di(4-methoxyphenyl)iodonium hexafluorophosphate; di(3-carboxyphenyl)iodonium hexafluorophosphate; di(3-methoxycarbonylphenyl)iodonium hexafluorophosphate; di(3-methoxysulfonylphenyl)iodonium hexafluorophosphate; di(4-acetamidophenyl)iodonium hexafluorophosphate; di(2-benzothienyl)iodonium hexafluorophosphate; and diphenyliodonium hexafluoroantimonate.

Of the aromatic iodonium complex salts which are suitable for use in the compositions of the invention diaryliodonium hexafluorophosphate, diaryliodonium hexafluoroantimonate, 4-octyloxyphenyl phenyliodonium hexafluoroantimonate, 4-(2-hydroxytetradecyloxyphenyl) phenyliodonium hexafluoroantimonate, and 4-(1-methylethyl)phenyl 4-methylphenyliodonium tetrakis (pentafluorophenyl)borate are among the preferred salts. These salts are preferred because, in general, they promote faster reaction, and are more soluble in inert organic solvents than are other aromatic iodonium salts of complex ions.

The aromatic iodonium complex salts may be prepared by metathesis of corresponding aromatic iodonium simple salts (such as, for example, diphenyliodonium bisulfate) in accordance with the teachings of Beringer et al., *J. Am. Chem. Soc.* 81, 342 (1959). Thus, for example, the complex salt diphenyliodonium tetrafluoroborate is prepared by the addition at 60° C. of an aqueous solution containing 29.2 g silver fluoroborate, 2 g fluoroboric acid, and 0.5 g phosphorous acid in about 30 ml of water to a solution of 44 g (139 millimoles) of diphenyliodonium chloride. The silver halide that precipitates is filtered off and the filtrate concentrated to yield diphenyliodonium fluoroborate which may be purified by recrystallization.

The aromatic iodonium simple salts may be prepared in accordance with Beringer et al., above, by various methods including (1) coupling of two aromatic compounds with iodyl sulfate in sulfuric acid, (2) coupling of two aromatic compounds with an iodate in acetic acid-acetic anhydride-sulfuric acid, (3) coupling of two aromatic compounds with an iodine acrylate in the presence of an acid, and (4) condensation of an iodoso compound, an iodoso diacetate, or an iodoxy compound with another aromatic compound in the presence of an acid. Diphenyliodonium bisulfate is prepared by method (3), for example, by the addition over a period of eight hours at below 5° C. of a mixture of 35 ml of conc. sulfuric acid and 50 ml of acetic anhydride to a well-stirred mixture of 55.5 ml of benzene, 50 ml of acetic anhydride, and 53.5 g of potassium iodate. The mixture is stirred for an additional four hours at 0°–5° C. and at room temperature (about 25° C.) for 48 hours and treated with 300 ml of diethyl ether. On concentration, crude diphenyliodonium bisulfate precipitates and may be purified by recrystallization if desired.

The second component in the photoinitiator system is a visible light sensitizer. The visible light sensitizer should be partly or fully soluble in the photopolymerizable composition, free of functionalities that would substantially interfere with the cationic polymerization process, and capable of light absorption somewhere within the range of wavelengths between about 400 and about 1000 nanometers. Preferred visible light sensitizers contain one or more carbonyl functional groups.

Suitable visible light sensitizers may include compounds in the following categories: ketones, coumarin dyes (e.g., ketocoumarins), xanthene dyes, fluorone dyes, fluorescein dyes, aminoketone dyes, and p-substituted aminostyryl ketone compounds. Ketones (e.g., monoketones or alpha-diketones), coumarin dyes (e.g., ketocoumarins), xanthene dyes, fluorone dyes, and fluorescein dyes are particularly preferred visible light sensitizers for use in the invention. For applications requiring deep cure (e.g., cure of highly-filled composites), it is preferred to employ sensitizers having an extinction coefficient below about 1000 lmole$^{-1}$cm$^{-1}$, more preferably about or below 100 lmole$^{-1}$cm$^{-1}$, at the desired wavelength of irradiation for photopolymerization. The alpha-diketones are an example of a class of visible light sensitizers having this property, and are particularly preferred for dental applications. Deep cure can also be achieved utilizing visible light sensitizers with an extinction coefficient greater than 1000 lmole$^{-1}$cm$^{-1}$, if the sensitizer exhibits a decreasing extinction coefficient upon exposure to light. The xanthene dyes, fluorone dyes, and fluorescein dyes are examples of a class of visible light sensitizers having this property.

By way of example, a preferred class of ketone visible light sensitizers has the formula:

where X is CO or CR$^1$R$^2$ where R$^1$ and R$^2$ can be the same or different, and can be hydrogen, alkyl, alkaryl or aralkyl, b is zero, and A and B can be the same or different and can be substituted (having one or more non-interfering substituents) or unsubstituted aryl, alkyl, alkaryl, or aralkyl groups, or together A and B can form a cyclic structure which can be a substituted or unsubstituted cycloaliphatic, aromatic, heteroaromatic or fused aromatic ring.

Suitable ketones of the above formula include monoketones (b=0) such as 2,2-, 4,4- or 2,4-dihydroxybenzophenone, di-2-pyridyl ketone, di-2-furanyl ketone, di-2-thiophenyl ketone, benzoin, fluorenone, chalcone, Michler's ketone, 2-fluoro-9-fluorenone, 2-chlorothioxanthone, acetophenone, benzophenone, 1- or 2-acetonaphthone, 9-acetylanthracene, 2-, 3- or 9-acetylphenanthrene, 4-acetylbiphenyl, propiophenone, n-butyrophenone, valerophenone, 2-, 3- or 4-acetylpyridine, 3-acetylcoumarin and the like. Suitable diketones include aralkyldiketones such as anthraquinone, phenanthrenequinone, o-, m- and p-diacetylbenzene, 1,3-, 1,4-, 1,5-, 1,6-, 1,7- and 1,8-diacetylnaphthalene, 1,5-, 1,8- and 9,10-diacetylanthracene, and the like. Suitable 1-diketones (b=1 and x=CO) include 2,3-butanedione, 2,3-pentanedione, 2,3-hexanedione, 3,4-hexanedione, 2,3-heptanedione, 3,4-heptanedione, 2,3-octanedione, 4,5-octanedione, benzil, 2,2'- 3 3'- and 4,4'-dihydroxylbenzyl, furil, di-3,3'-indolylethanedione, 2,3-bomanedione (camphorquinone), biacetyl, 1,2-cyclohexanedione, 1,2-naphthaquinone, acenaphthaquinone, 1-phenyl- 1,2-propanedione, and the like.

Examples of particularly preferred visible light sensitizers include the alpha-diketones: camphorquinone; glyoxal; biacetyl; 3,3,6,6-tetramethylcyclohexanedione; 3,3,7,7-tetramethyl-1,2-cycloheptanedione; 3,3,8,8-tetramethyl-1,2-cyclooctanedione; 3,3,18,18-tetramethyl-1,2-cyclooctadecanedione; dipivaloyl; benzil; furil; hydroxybenzil; 2,3-butanedione; 2,3-pentanedione; 2,3-hexanedione; 3,4-hexanedione; 2,3-heptanedione; 3,4-heptanedione; 2,3-octanedione; 4,5-octanedione; 1,2-cyclohexanedione; and 1-phenyl-1,2-propanedione. Of these, camphorquinone is the most preferred visible light sensitizer.

Examples of preferred fluorone dyes include, but are not limited to, fluorescein, 4'5'-dibromofluorescein, erythrosin B, ethyl eosin, eosin Y, and erythrosin, yellowish blend.

The third component in the photoinitiator system is an electron donor compound. A wide variety of electron donor compounds can be employed in the practice of the invention, and generally are capable of increasing the speed of polymerization and/or the depth of polymerization of a composition according to the invention when exposed to visible light of the desired wavelength, as compared to the same composition but excluding the electron donor compound.

Preferred electron donor compounds for use in the invention possess one or more (and more preferably several if not all) of the following properties: (a) they are soluble in the polymerizable composition; (b) they do not absorb a significant amount of light at the wavelength of the light used to photopolymerize the composition, typically the wavelength at which the visible light sensitizer exhibits maximum absorption, by which it is meant that the electron donor compound does not detrimentally affect the performance of the visible light sensitizer; (c) they have an oxidation potential (E$_{ox}$) greater than 0 but less than that of 1,4-dimethoxybenzene when measured versus a saturated calomel electrode (SCE); (d) they yield a photoinitiator system that has a photoinduced potential less than that of 3-dimethylaminobenzoic acid in a standard solution of 2.9×10$^{-5}$ moles/g diphenyl iodonium hexafluoroantimonate and 1.5×10$^{-5}$ moles/g camphorquinone in 2-butanone; (e) a pk$_b$ greater than 8; (f) they impart not more than a minimal amount of objectionable color to the polymerized resin; (g) they impart not more than a minimal amount of objectionable fluorescence to the polymerized resin; (h) they cause no more than a minimal amount of polymerization inhibition; (i) they improve the shelf life stability of the polymerizable composition; and (j) they can be used in a lower effective concentration than other polymerization aids. Other factors that may influence the selection of the electron donor compound for a particular composition include the cationically polymerizable resin, the iodonium salt, and the visible light sensitizer that have been chosen, as well as the shelf stability of the cationically polymerizable composition.

While preferred electron donor compounds for use in the invention have an E$_{ox}$ greater than zero and less than or equal to that of 1,4-dimethoxybenzene, it is more preferred that the electron donor compound have an E$_{ox}$ that is less than about 1.35 volts when measured using a saturated calomel electrode (SCE), and even more preferred that the E$_{ox}$ be between about 0.5 and 1.34 volts (vs. a SCE). E$_{ox}$ values can be measured experimentally, or obtained from established reference sources, such as N. L. Weinburg, Ed., *Technique of Electroorganic Synthesis Part II Techniques of*

*Chemistry*, Vol. V (1975), and C. K. Mann and K. K. Barnes, *Electrochemical Reactions in Nonaqueous Systems* (1970).

As noted hereinabove, preferred electron donor compounds for use in the invention yield a photoinitiator system that has a photoinduced potential less than that of 3-dimethylaminobenzoic acid in a standard solution of $2.9 \times 10^{-5}$ moles/g diphenyl iodonium hexafluoroantimonate and $1.5 \times 10^{-5}$ moles/g camphorquinone in 2-butanone. Generally, 3-dimethylamino benzoic acid exhibits a photoinduced potential of at least about 115 mV when measured in this standard solution.

The photoinduced potential can be evaluated by comparing the photoinduced potential of a photoinitiator system that includes the electron donor compound of interest as compared to a photoinitiator system that employs 3-dimethylaminobenzoic acid. More specifically, a standard solution of $2.9 \times 10^{-5}$ moles/g diphenyl iodonium hexafluoroantimonate, $1.5 \times 10^{-5}$ moles/g camphorquinone, and $2.9 \times 10^{-5}$ moles/g of 3-dimethylaminobenzoic acid in 2-butanone is prepared. A pH electrode is then immersed in the solution and the pH meter is calibrated to zero mV. The standard solution is irradiated with blue light having a wavelength of between about 400 to 500 nm and an intensity of about 200 to 400 mW/cm² for about 5 to 10 seconds using a focused light source such as a commercially available dental curing light. After light exposure, the photoinduced potential of the standard solution is measured by immersing the pH electrode in the irradiated standard solution and recording the photoinduced potential in mV using the pH meter. A test solution is then prepared containing $2.9 \times 10^{-5}$ moles/g of diphenyl iodonium hexafluoroantimonate, $1.5 \times 10^{-5}$ moles/g of camphorquinone, and $2.9 \times 10^{-5}$ moles/g of the electron donor compound of interest in 2-butanone. The test solution is irradiated and the photoinduced potential measured using the same technique as described for the standard solution. If the test solution has a photoinduced potential that is less than that of the standard solution containing 3-dimethylaminobenzoic acid, then the compound is considered to be a particularly preferred electron donor for use in the invention.

One class of electron donor compounds useful in photoinitiator systems according to the invention comprises polycyclic aromatic compounds (i.e., polycyclic compounds having two or more fused aromatic rings), including their alkyl- and aryl-substituted derivatives. By "fused" is meant two aromatic rings with a shared side or with opposing sides directly joined by carbon-carbon bonds.

Representative classes of useful polycyclic aromatic electron donor compounds include, but are not limited to, biphenylenes, naphthalenes, anthracenes, benzanthracenes, pyrenes, azulenes, pentacenes, decacyclenes, and derivatives (such as acenaphthenes) and combinations thereof.

More specifically, electron donor compounds conforming to the structures shown below may be employed.

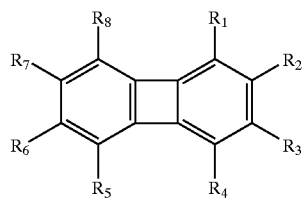

-continued

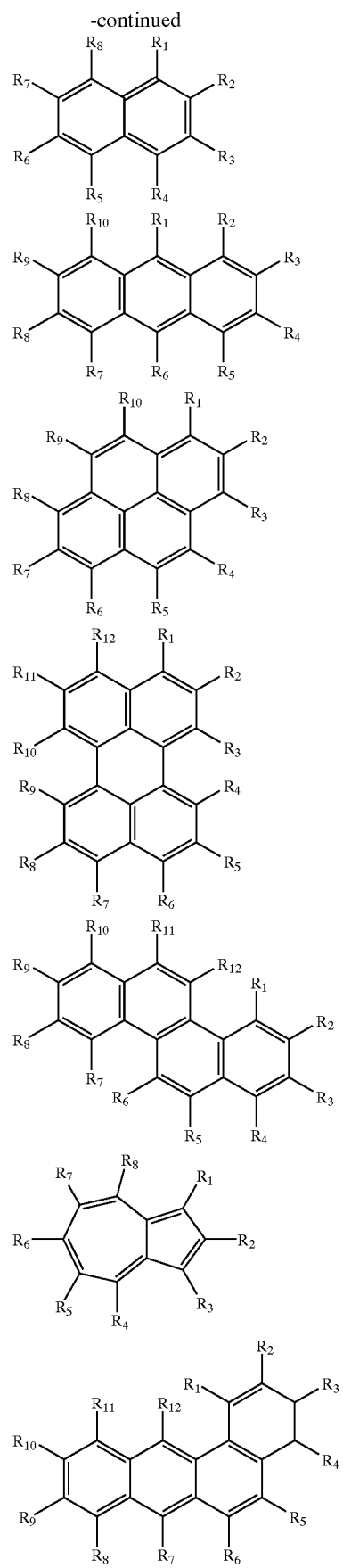

-continued

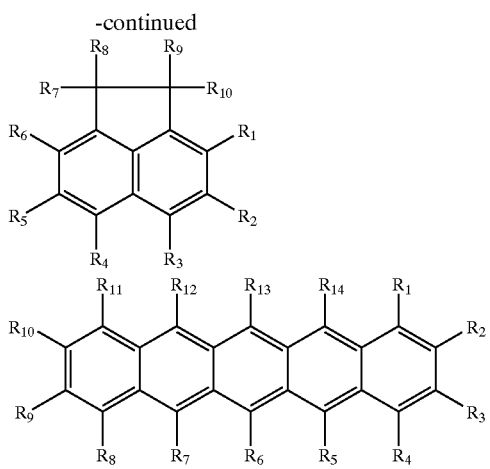

In the foregoing structures, the substituents $R_1$ to $R_{14}$ may be any group that does not have a substantially adverse effect on cationic polymerization, and preferably are independently selected from H or hydrocarbon groups. The hydrocarbon groups may be alkyl groups (e.g., $C_{1-10}$ alkyl, $C_{2-10}$ alkenyl, or $C_{3-10}$ cycloalkyl groups) or aromatic groups (e.g., $C_{5-10}$ aromatic groups). The hydrocarbon groups can be optionally substituted by one or more halogen, —CN, —OH, —SH, —COOH, —COO$C_{1-10}$ alkyl, —($C_{1-10}$ alkyl)$_{0-1}$—COH, —($C_{1-10}$ alkyl)$_{0-1}$—CO—$C_{1-10}$ alkyl, as well as other hydrocarbon groups. The various R-group substituents may also cooperate to form an aromatic or cycloalkyl ring. The most preferred R-group substituents are methyl, ethyl, vinyl and phenyl.

Particularly useful polycyclic aromatic electron donor compounds include: biphenylene, anthracene, 9-methylanthracene, 9-vinyl anthracene, 9-phenylanthracene, 9,10-diphenylanthracene, 9,10-dimethylanthracene, 2-ethylanthracene, acenaphthene, pyrene, pentacene, decacyclene, azulene, 7,12-dimethyl-1,2-benzanthracene, 1,2-benzanthracene, 1,4-dimethylnaphthalene, 2,3,5-trimethylnaphthalene, and combinations thereof. All of these compounds are available from Sigma-Aldrich, St. Louis, Mo.

Another class of electron donor compounds that may be useful in photoinitiator systems according to the invention includes N-alkyl carbazole derivatives having the following formula:

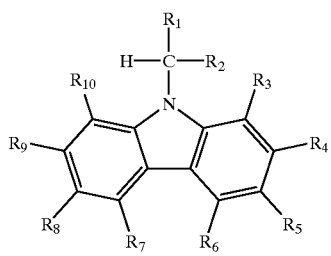

In the foregoing structure, the substituents $R_1$ to $R_{10}$ may be any group that does not have a substantially adverse effect on cationic polymerization, and preferably are independently selected from H or hydrocarbon groups. The hydrocarbon groups may be alkyl groups (e.g., $C_{1-10}$ alkyl, $C_{2-10}$ alkenyl or $C_{3-10}$ cycloalkyl groups) or aromatic groups (e.g., $C_{5-10}$ aromatic groups). The hydrocarbon groups can be optionally substituted by one or more halogen, —CN, —OH, —SH, —COOH, —COO$C_{1-10}$ alkyl, —($C_{1-10}$ alkyl)$_{0-1}$—COH, —($C_{1-10}$ alkyl)$_{0-1}$—CO— $C_{1-10}$ alkyl, as well as other hydrocarbon groups. The various R-group substituents may also cooperate to form an aromatic or cycloalkyl ring or a low basicity heterocyclic ring. Other possible substituents include alkyl or aromatic ethers, carboxylic acids and esters, nitrites, aldehydes, ketones and other groups that do not significantly interfere with cationic polymerization.

A preferred N-alkyl carbazole compound is N-methyl carbazole available from Sigma-Aldrich, St. Louis, Mo.

Advantageously, the electron donor compound may accelerate the rate of polymerization (as measured by gel time) of the cationically polymerizable resin, as compared to compositions without the electron donor compound. For many uses of the photopolymerizable compositions, the gel time is preferably less than 60 minutes, more preferably less than about 10 minutes, and most preferably less than about 2 minutes as established according to the following gel time protocol. The electron donor compound and comparative compounds were evaluated for their effect on the polymerization speed in a particular cationically polymerizable composition by combining the cationically polymerizable resin with the desired visible light sensitizer, iodonium salt, and electron donor compound, and mixing until homogeneous. Each sample was examined for gel time by transferring the photopolymerizable composition to a 6-mm diameter×2.5-mm thick Teflon mold with a polyester film clamped in direct contact with the bottom face. The sample was placed directly beneath the light guide of a VISILUX 2 or ELIPAR Trilight (utilizing the standard light intensity mode for the latter) dental curing light at a distance of 10 mm. Samples were irradiated up to a maximum of 120 seconds and hard gel times were established by probing the surface with a plastic probe until a hard, tack free surface was observed.

The individual components of the ternary photoinitiator system are provided in photopolymerizingly effective amounts (i.e., amounts effective to yield a photoinitiator system that can initiate photopolymerization of the cationically polymerizable resin or, more preferably, that can accelerate the rate of polymerization). Preferably, the visible light sensitizer is present at about 0.05–5.0 weight percent based on the overall photopolymerizable composition, more preferably, at about 0.10–2.0 weight percent. The iodonium salt is preferably present at about 0.05–10.0 weight percent, more preferably at about 0.10–5.0 weight percent, and most preferably at about 0.50–3.0 weight percent, based on the overall composition. The electron donor compound is preferably present at about 0.01–5.0 weight percent, more preferably about 0.05–1.0 weight percent, and most preferably about 0.05–0.50 weight percent, based on the overall composition.

The photopolymerizable compositions of the invention are prepared by simply admixing, under "safe light" conditions, the components of the inventive compositions. Suitable inert solvents may be employed if desired when effecting this mixture. Any solvent may be used which does not react appreciably with the components of the inventive compositions. Examples of suitable solvents include acetone, dichloromethane, acetonitrile and lactones. A liquid material to be polymerized may be used as a solvent for another liquid or solid material to be polymerized. Solventless compositions can be prepared by simply dissolving the iodonium complex salt, sensitizer, and electron donor in the cationically polymerizable resin, with or without the use of mild heating to facilitate dissolution.

The compositions of the present invention provide a very useful combination of polymerization speed, polymerization depth, and shelf life. They polymerize well even when loaded with large amounts of filler, and can be used in a variety of applications including graphic arts imaging (e.g., for color proofing systems, curable inks, or silverless imaging), printing plates (e.g., projection plates or laser plates), photoresists, solder masks, electronic conformal coatings and underfills, optical fiber coatings, coated abrasives, magnetic media, photocurable adhesives (e.g. for orthodontic, electronic, fiber optic and medical applications etc ), hardcoats (e.g., for optical lenses), and photocurable composites (e.g., for autobody repair or dentistry). Dental, electronics, optical lenses, and optical fiber applications particularly benefit from the unique compositions of the present invention.

Acrylate- and methacrylate-based materials have been commonly used for adhesive and restorative dental compositions. These materials offer the advantage of being polymerizable with visible light using photoinitiator systems, but have the disadvantage of undergoing a relatively high degree of shrinkage during the polymerization process. In contrast, the cationically polymerizable resins found in the compositions of the present invention shrink significantly less than acrylate or methacrylate resins during polymerization. The present invention provides a system for polymerizing cationically polymerizable resins in an acceptable time frame, e.g., less than 120 seconds, and to a sufficient depth using visible light source equipment already available in the dental office or electronics fabrication facilities.

The compositions of the invention are particularly well adapted for use as a wide variety of dental materials, which may be filled or unfilled. Such dental materials include direct esthetic restorative materials (e.g., anterior and posterior restoratives), prostheses, adhesives and primers for oral hard tissues, sealants, veneers, cavity liners, orthodontic bracket adhesives for use with any type of bracket (such as metal, plastic and ceramic), crown and bridge cements, artificial crowns, artificial teeth, dentures, and the like. These dental materials are used in the mouth and are disposed adjacent to natural teeth. The phrase "disposed adjacent to" as used herein refers to the placing of a dental material in temporary or permanent bonding (e.g., adhesive) or touching (e.g., occlusal or proximal) contact with a natural tooth. The term "composite" as used herein in the context of a dental material refers to a filled dental material. The term "restorative" as used herein refers to a dental composite that is polymerized after it is disposed adjacent to a tooth. The term "prosthesis" as used herein refers to a composite that is shaped and polymerized for its final use (e.g., as a crown, bridge, veneer, inlay, onlay or the like) before it is disposed adjacent to a tooth. The term "sealant" as used herein refers to a lightly filled dental composite or to an unfilled dental material that is cured after it is disposed adjacent to a tooth.

In certain dental applications, the use of a filler may be appropriate. The choice of the filler affects important properties of the dental composite such as its appearance, radiopacity and physical and mechanical properties. Appearance is affected in part by adjustment of the amounts and relative refractive indices of the ingredients of the composite, thereby allowing alteration of the translucence, opacity or pearlescence of the composite. Cationically polymerizable compositions of the invention can be prepared with refractive indices which approach or approximate the refractive indices of fillers such as quartz (refractive index 1.55), submicron silica (refractive index 1.46), and 5.5:1 mole ratio SiO:ZrO, non-vitreous microparticles (refractive index 1.54). In this way, the appearance of the dental material can, if desired, be made to closely approximate the appearance of natural dentition.

Radiopacity is a measurement of the ability of the dental composite to be detected by x-ray examination. Frequently a radiopaque dental composite will be desirable, for instance, to enable the dentist to determine whether or not a dental restoration remains sound. Under other circumstances a non-radiopaque composite may be desirable. Suitable fillers for radiopaque formulations are described in EP-A2-0 189 540, EP-B-0 238 025, and U.S. Pat. No. 6,306,926B1.

The amount of filler which is incorporated into the composite, referred to herein as the "loading level" and expressed as a weight percent based on the total weight of the dental material, will vary depending on the type of filler, the cationically curable resin and other components of the composition, and the end use of the composite.

For some dental materials, such as sealants, the cationically polymerizable compositions of the invention can be lightly filled (e.g., having a loading level of less than about 40 weight percent) or unfilled. Preferably the viscosity of the dental material is sufficiently low to allow its penetration into pits and fissures of occlusal tooth surfaces as well as into etched areas of enamel, thereby aiding in the retention of the dental material. In applications where high strength or durability are desired (e.g., anterior or posterior restoratives, prostheses, crown and bridge cements, artificial crowns, artificial teeth and dentures) the loading level can be as high as about 95 weight percent. For most dental restorative and prosthetic applications a loading level of between about 60 and 90 weight percent is generally preferred.

Fillers may be selected from one or more of any material suitable for incorporation in compositions used for medical applications, such as fillers currently used in dental restorative compositions and the like. The filler is finely divided and preferably has a maximum particle diameter of less than about 50 micrometers and an average particle diameter of less than about 10 micrometers. The filler can have a unimodal or polymodal (e.g., bimodal) particle size distribution. The filler can be an inorganic material. It can also be a crosslinked organic material that is insoluble in the polymerizable resin, and is optionally filled with inorganic filter. The filler should in any event be non-toxic and suitable for use in the mouth. The filler can be radiopaque, radiolucent or nonradiopaque.

Examples of suitable inorganic fillers are naturally-occurring or synthetic materials such as quartz, nitrides (e.g., silicon nitride), glasses derived from, for example Ce, Sb, Sn, Zr, Sr, Ba and Al, colloidal silica, feldspar, borosilicate glass, kaolin, talc, titania, and zinc glass; low Mohs hardness fillers such as those described in U.S. Pat. No. 4,695,251; and submicron silica particles (e.g., pyrogenic silicas such as the "Aerosil" Series "OX 50", "130", "150" and "200" silicas sold by Degussa and "Cab-O-Sil M5" silica sold by Cabot Corp.). Examples of suitable organic filler particles include filled or unfilled pulverized polycarbonates, polyepoxides, and the like. Preferred filler particles are quartz, submicron silica, and non-vitreous microparticles of the type described in U.S. Pat. No. 4,503,169. Metallic fillers may also be incorporated, such as particulate metal filler made from a pure metal such as those of Groups IVA, VA, VIA, VIIA, VIU, IB, or IIB, aluminum, indium, and thallium of Group IIIB, and tin and lead of Group IVB, or alloys thereof. Conventional dental amalgam alloy powders, typically mixtures of silver, tin, copper, and zinc, may also optionally be incorporated. The particulate metallic filler preferably has an average particle size of about 1 micron to about 100 microns, more preferably 1 micron to about 50 microns. Mixtures of these fillers are also contemplated, as well as combination fillers made from organic and inorganic materials. Fluoroaluminosilicate glass fillers, either untreated or silanol treated, are particularly preferred. These glass fillers have the added benefit of releasing fluoride at the site of dental work when placed in the oral environment.

Optionally, the surface of the filler particles may be treated with a surface treatment such as a coupling agent in order to enhance the bond between the filler and the polymerizable resin. The coupling agent may be functionalized with reactive curing groups, such as acrylates, methacrylates, epoxies, and the like. Examples of coupling agents include silanes such as gamma-methacryloxypropyltrimethoxysilane, gamma-mercaptopropyltriethoxysilane, beta-(3,4-epoxycyclohexyl) ethyltrimethoxysilane, gamma-glycidoxypropyltrimethoxysilane, and the like.

The materials of the present invention can also contain suitable adjuvants such as accelerators, inhibitors, absorbers, stabilizers, pigments, dyes, viscosity modifiers, surface tension depressants and wetting aids, antioxidants, and other ingredients well known to those skilled in the art.

The amounts and types of each ingredient in the dental material should be adjusted to provide the desired physical and handling properties before and after polymerization. For example, the polymerization rate, polymerization stability, fluidity, compressive strength, tensile strength and durability of the dental material typically are adjusted in part by altering the types and amounts of polymerization initiator(s) and, if present, the loading and particle size distribution of filler(s). Such adjustments typically are carried out empirically based on experience with dental materials of the prior art.

When the dental material is applied to a tooth, the tooth can optionally be pre-treated with a primer such as dentin or enamel adhesive by methods known to those skilled in the art.

The invention is further described by reference to the following examples, which are understood to be merely illustrative and not limiting the invention in any way.

EXAMPLES

Example 1

A first stock resin solution (Matrix 1) of an epoxy resin material was prepared by combining 0.50 g camphorquinone (CPQ), 1.50 g diphenyliodonium hexafluoroantimonate (DPI SbF$_6$) and 98.00 g UVR 6105 cycloaliphatic diepoxide (Union Carbide, Danbury, Conn.), and stirring in the absence of light until homogeneous. UVR 6105 is a cycloaliphatic diepoxide having the following formula:

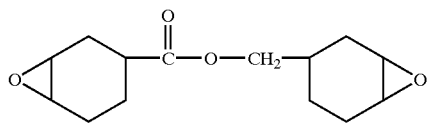

Additionally, a second stock resin solution (Matrix 2) was prepared in the absence of light by stirring 0.50 g CPQ, 2.00 g methyl-isopropyl-diphenyliodonium-tetrakispentafluorophenylborate (Rhodorsil PI 2074, Rhône-Poulenc, France), 48.75 g 3,4-epoxycyclohexyl-methyl-3,4-epoxycyclohexancarboxylate (Cyracure UVR 6105, Union Carbide, Danbury, Conn.) and 48.75 g of a mixture of 1,3,5,7-tetrakis(2,1-ethandiyl-3,4-epoxycyclohexyl)-1,3,5,7-tetramethylcyclo-tetrasiloxane and 1,3,5,7,9-pentakis(2,1-ethandiyl-3,4-epoxycyclohexyl)-1,3,5,7,9-pentamethylcyclopentasiloxane (synthesized according to Japanese Patent Publication No. 51-033541 in the Pt-catalyzed hydrosilylation reaction of vinylcyclohexene with a mixture of 1,3,5,7-tetramethylcyclo-tetrasiloxane and 1,3,5,7,9-pentamethylcyclopentasiloxane purchased from ABCR, Karlsruhe Germany in a 60:40 ratio).

A variety of polycyclic aromatic electron donor compounds and comparative compounds (test compounds) were evaluated for their photoinduced potential. To evaluate the photoinduced potential of the compounds, a stock initiator solution was prepared by transferring 0.50 g CPQ and 3.00 g of DPI SbF$_6$ to a 250-ml polyethylene screw-top bottle. 200 g of 99.5+% 2-butanone were transferred to the polyethylene bottle and the contents mixed until homogeneous. The resulting solution contained approximately $2.9 \times 10^{-5}$ moles DPISbF$_6$/gram of stock initiator solution, and $1.5 \times 10^{-5}$ moles CPQ/gram of stock initiator solution. The electron donor compounds were evaluated at a concentration of $2.9 \times 10^{-5}$ moles electron donor compound/gram of stock initiator solution. Test samples were prepared by transferring $1.16 \times 10^{-4}$ moles of the electron donor compound to a 13-ml glass vial followed by the addition of 4.0 g of the stock initiator solution. Vials were capped and vigorously shaken until homogeneous. Test samples were then evaluated for relative potential according to the following procedure:

A semi-micro combination pH electrode (Corning model 476540) was connected to a pH meter with millivolt capability (Beckman Φ P/N 123133). The stock initiator solution was used as the millivolt standard in this evaluation. Four grams of the stock initiator solution were transferred to a 13-ml glass vial along with a micro-magnetic stir bar. The sample was placed above a magnetic stirrer that initiated slow stirring of the sample. The electrode was rinsed with water followed by ethanol, and then thoroughly dried with a paper towel. The electrode was immersed in the stock initiator solution and the millivolt reading calibrated to read 0.00 mV. The electrode was removed and the sample (containing electron donor or comparative compound) was irradiated with a VISILUX dental curing light having an intensity of about 200 mW/cm$^2$ at a wavelength of 400 to 500 nm for 10 seconds by placing the tip of the light guide directly flush with the center bottom of the vial. Following irradiation the sample was capped and mixed thoroughly by shaking for about 5 seconds. The electrode was rinsed, cleaned thoroughly with ethanol, blotted dry and immersed in the irradiated solution. The millivolt reading relative to the control was established by pressing the mV button on the pH meter until a stable reading was obtained. The above procedure was repeated with the various test samples. The electrode was calibrated with unirradiated stock initiator solution before each run as described previously. The photoinduced potential results are shown in Table 1 along with the quantity of electron donor and comparative compounds tested (in grams of electron donor compound per four grams of stock initiator solution).

The electron donor and comparative compounds were evaluated for their affect on polymerization speed of one of the two described stock resin solutions (Matrix 1 and Matrix 2). Approximately one-gram samples were prepared by transferring $2.9 \times 10^{-5}$ moles of each prospective electron donor compound to 1-dram glass vials followed by 1 drop of chloromethane solvent and 1.0 gram of the respective stock resin solution. The ingredients were mixed until homogeneous. Each sample was examined for gel time by transferring the solution to a 6-mm diameter and 2.5-mm thick Teflon™ mold with a polyester film clamped in direct contact with the bottom face. The sample was placed directly beneath the light guide of a VISILUX 2 dental curing light at a distance of 10 mm. Samples were irradiated up to a maximum of 120 seconds and probed at the surface with a plastic probe until a hard, tack-free surface was observed to establish hard gel times. The gel time results are reported in Tables 2a (for Matrix 1 stock resin solution) and 2b (for Matrix 2 stock resin solution), along with the quantity of electron donor and comparative compounds tested (in grams of electron donor compound per gram of the respective stock resin solution). Also shown in Tables 2a and 2b are the calculated molecular weight (MW) values and the published oxidation potentials ($E_{ox}$) of the various electron donor and comparative compounds, as reported in N. L. Weinburg, Ed., *Technique of Electroorganic Synthesis Part II Techniques of Chemistry*, Vol. V (1975). Sample numbers preceded by the letter "C" refer to comparative samples.

TABLE 1

| Sample Number | Test Compound | Test Compound (g) Per Four Grams of Stock Initiator Solution (Matrix 1) | Photo-induced Potential (mV) (2-Butanol Solvent) |
|---|---|---|---|
| C | Control (No Test Compound) | none | 13 |
| C1 | 3-Dimethylaminobenzoic acid | 0.0191 | 111 |
| C2 | Ethyl 4-Dimethylaminobenzoate | 0.0224 | 173 |
| C3 | Naphthalene | 0.0148 | −25 |
| C4 | Phenanthrene | 0.0206 | −16 |
| 1 | 1,4-Dimethylnaphthalene | 0.0181 | 31 |
| 2 | 2,3,5-Trimethylnaphthalene | 0.0197 | NT |
| 3 | Biphenylene | 0.0176 | 13 |
| 4 | Acenaphthene | 0.0179 | −15 |
| 5 | Pyrene | 0.0234 | −12 |
| 6 | Anthracene | 0.0206 | −21 |
| 7 | Azulene | 0.0148 | −32 |
| 8 | 9,10-Dimethylanthracene | 0.0239 | 81 |
| 9 | Pentacene | 0.0322 | 3 |

NT—Not Tested

TABLE 2a

| Sample Number | Test Compound | $E_{ox}$ | MW | Test Compound (g) Per Gram of Stock Resin Solution (Matrix 1) | Gel Time (Sec) |
|---|---|---|---|---|---|
| C | Control (No Test Compound) | — | — | None | Not cured after 120 seconds |
| C1 | 3-Dimethylaminobenzoic acid | 1.07 | 165 | 0.0047 | 17 |
| C2 | Ethyl 4-Dimethylaminobenzoate | 1.07 | 193 | 0.0056 | 8 |
| C3 | Naphthalene | 1.54 | 128 | 0.0037 | Not cured after 120 seconds |
| C4 | Phenanthrene | 1.50 | 178 | 0.0052 | Not cured after 120 seconds |
| 1 | 1,4-Dimethylnaphthalene | NP | 156 | 0.0045 | Partially cured after 120 seconds |
| 2 | 2,3,5-Trimethylnaphthalene | NP | 170 | 0.0049 | Partially cured after 120 seconds |
| 3 | Biphenylene | 1.30 | 152 | 0.0044 | 10 |
| 4 | Acenaphthene | 1.21 | 154 | 0.0045 | 19 |
| 5 | Pyrene | 1.16 | 202 | 0.0059 | 9 |
| 6 | Anthracene | 1.09 | 178 | 0.0052 | 15 |
| 7 | Azulene | 0.71 | 128 | 0.0037 | 80 |
| 8 | 9,10-Dimethylanthracene | 0.65 | 206 | 0.0060 | 6 |
| 9 | Pentacene | NP | 278 | 0.0081 | 67 |

NP- $E_{ox}$ values not published in reference source.

TABLE 2b

| Sample Number | Test Compound | $E_{ox}$ | MW | Test Compound (g) Per Gram of Stock Resin Solution (Matrix 2) | Gel Time (Sec) |
|---|---|---|---|---|---|
| C | Control (No Test Compound) | — | — | None | 22 |
| C1 | 3-Dimethylaminobenzoic acid | 1.07 | 165 | 0.0047 | 16 |
| C4 | Phenanthrene | 1.50 | 178 | 0.0055 | 22 |
| C5 | 2-methyl-naphthalene | 1.55 | 142 | 0.0045 | 22 |
| 3 | Biphenylene | 1.30 | 152 | 0.005 | 3 |
| 3a | Biphenylene | 1.30 | 152 | 0.00002 | 10 |
| 4 | Acenaphthene | 1.21 | 154 | 0.00475 | 20 |
| 5 | Pyrene | 1.16 | 202 | 0.005 | 3 |
| 6 | Anthracene | 1.09 | 178 | 0.0055 | 7 |
| 6a | Anthracene | 1.09 | 178 | 0.00011 | 4 |
| 7 | Azulene | 0.71 | 128 | 0.0017 | 18 |
| 8 | 9,10-Dimethylanthracene | 0.65 | 206 | 0.0065 | 2 |
| 9 | Pentacene | NP | 278 | 0.0085 | 22 |
| 11 | 9-methyl-anthracene | 0.96 | 192 | 0.0055 | 3 |
| 11a | 9-methyl-anthracene | 0.96 | 192 | 0.0011 | 3 |
| 12 | 2-ethyl-anthracene | NP | 206 | 0.0065 | 4 |
| 13 | 9-vinyl-anthracene | NP | 204 | 0.0065 | 5 |
| 13a | 9-vinyl-anthracene | NP | 204 | 0.0013 | 9 |
| 14 | 9-phenyl-anthracene | 1.0 | 254 | 0.0075 | 5 |
| 14a | 9-phenyl-anthracene | 1.0 | 254 | 0.0015 | 4 |
| 15 | 9,10-diphenyl-anthracene | 0.9 | 330 | 0.01 | 3 |
| 15a | 9,10-diphenyl-anthracene | 0.9 | 330 | 0.002 | 4 |
| 16 | 1,2-benzanthracene | 1.33 | 228 | 0.007 | 3 |
| 16a | 1,2-benzanthracene | 1.33 | 228 | 0.0014 | 3 |
| 17 | 7,12-dimethyl-1,2-benzanthracene | 1.1 | 228 | 0.008 | 3 |
| 17a | 7,12-dimethyl-1,2-benzanthracene | 1.1 | 228 | 0.0016 | 2 |
| 18 | 1,2,5,6-dibenzanthracene | 1.2 | 278 | 0.0085 | 3 |
| 18a | 1,2,5,6-dibenzanthracene | 1.2 | 278 | 0.0017 | 4 |

TABLE 2b-continued

| Sample Number | Test Compound | $E_{ox}$ | MW | Test Compound (g) Per Gram of Stock Resin Solution (Matrix 2) | Gel Time (Sec) |
|---|---|---|---|---|---|
| 19 | decacyclene | NP | 451 | 0.00275 | 8 |
| 19a | decacyclene | NP | 451 | 0.000275 | 7 |

NP- $E_{ox}$ values not published in reference source.

TABLE 3

| Sample Number | Test Compound | Test Compound (g) per Four Grams of Stock Initiator Solution (Matrix 1) | Photoinduced Potential (mV) (2-Butanol Solvent) |
|---|---|---|---|
| C | Control (No Test Compound) | none | 11 |
| C1 | 3-Dimethylaminobenzoic acid | 0.0191 | 168 |

TABLE 3-continued

| Sample Number | Test Compound | Test Compound (g) per Four Grams of Stock Initiator Solution (Matrix 1) | Photoinduced Potential (mV) (2-Butanol Solvent) |
|---|---|---|---|
| C2 | Ethyl 4-Dimethylaminobenzoate | 0.0224 | 232 |
| 1 | N-Methylcarbazole | 0.0206 | −176 |

TABLE 4

| Sample Number | Test Compound | $E_{ox}$ | MW | Test Compound (g) per Gram of Stock Resin Solution | Gel Time (Sec) | Matrix |
|---|---|---|---|---|---|---|
| C1 | Control (No Test Compound) | — | — | None | Not cured after 120 seconds | 1 |
| C1a | 3-Dimethylaminobenzoic acid | 1.07 | 165 | 0.0047 | 17 | 1 |
| 1 | N-Methylcarbazole | 1.10 | 181 | 0.0052 | 9 | 1 |
| C2 | Control (No Test Compound) | — | — | None | 22 | 2 |
| C2a | 3-Dimethylaminobenzoic acid | 1.07 | 165 | 0.0047 | 16 | 2 |
| 2 | N-Methylcarbazole | 1.10 | 181 | 0.0055 | 6 | 2 |

The data of Tables 1, 2a and 2b illustrate that a variety of polycyclic aromatic electron donor compounds can increase the polymerization speed of a cationically polymerizable resin (e.g., an epoxy resin) in the presence of a visible light sensitizer (e.g., CPQ) and an iodonium salt (e.g, DPI SbF$_6$). Surprisingly, the polycyclic aromatic electron donor compounds exhibit a high acceleration of polymerization speed (as measured by gel time reduction) even in very low concentrations while having a photoinduced potential less than that of 3-dimethylaminobenzoic acid. These electron donor compounds, with or without low extinction in the visible spectrum, can provide compositions having high utility as dental materials.

Example 2

In Example 2 the utility of carbazole compounds as electron donor compounds in the practice of the invention was evaluated. More specifically, the electron donor compound N-methylcarbazole was evaluated for its photoinduced potential and affect on epoxy resin polymerization speed as described in conjunction with Example 1. The results are shown in Tables 3 and 4.

The data of Tables 3 and 4 illustrate that carbazole compounds (e.g., N-methylcarbazole) can serve as effective electron donor compounds for enhancing the polymerization speed of a cationically polymerizable resin (e.g., an epoxy resin) in the presence of a visible light sensitizer (e.g., CPQ) and an iodonium salt (e.g., DPI SbF$_6$) while having a photoinduced potential less than that of 3-dimethylaminobenzoic acid.

Example 3

Dental filling materials were prepared by mixing in the absence of light the following components: 0.05 g CPQ; an electron donor in the amount shown in Table 5; 0.3 g methyl-isopropyl-diphenyliodonium-tetrakispentafluorophenylborate (Rhodorsil PI 2074,); 4.6 g 3,4-epoxycyclohexyl-methyl-3,4-epoxycyclohexancarboxylate (Cyracure UVR 6105,); 4.6 g of a mixture of 1,3,5,7-tetrakis(2,1-ethandiyl-3,4-epoxycyclohexyl)-1,3,5,7-tetramethylcyclo-tetrasiloxane and 1,3,5,7,9-pentakis(2,1-ethandiyl-3,4-epoxycyclohexyl)-1,3,5,7,9-pentamethylcyclopentasiloxane (synthesized according to Japanese Patent Publication No. 51-033541 in the Pt-catalyzed hydrosilylation reaction of vinylcyclohexene with a mixture of 1,3,5,7-tetramethylcyclo-tetrasiloxane and 1,3,5,7,9-pentamethylcyclopentasiloxane and purchased from ABCR, Karlsruhe Germany in a 60:40 ratio); and 0.3 g polytetrahydrofuran with an average molecular weight of 250 (Sigma-Aldrich). The resulting solution was mixed with 30.0 g of a quartz filler (silanated; less than 1 micron particle size) to afford a high-viscous paste. The paste was cured according to ISO 4049 with an ELIPAR Trilight dental curing device operating in the standard mode. The resulting hard material was then tested for Flexural Strength (FS) and Elastic Modulus (EM) according to ISO 4049 with the results shown in Table 5.

TABLE 5

| | | Electron Donor Compound | | |
|---|---|---|---|---|
| Test | None | Ethyl 4-Dimethylaminobenzoate (0.04 g) | Anthracene (0.01 g) | Biphenylene (0.02 g) |
| FS [MPa] | No cure | 109 ± 22 | 136 ± 23 | 131 ± 17 |
| EM [GPa] | No cure | 11.4 ± 0.1 | 12.0 ± 0.9 | 11.8 ± 0.6 |

The data shown in Table 5 indicate that the composite materials containing polycyclic aromatic electron donor compounds (e.g., anthracene or biphenylene) exhibit excellent cured (i.e., post-polymerization) physical properties as compared to a comparative composition that was polymerized in the absence of an electron donor compound. The data also show that polymerizable compositions containing the electron donor compounds anthracene and biphenylene provide slightly improved cured physical properties at a lower effective concentration as compared to a comparative composition that contains the electron donor compound ethyl 4-dimethylaminobenzoate (which yields a system that has a photoinduced potential greater than that of 3-dimethylaminobenzoic acid).

The above specification, examples and data provide a complete description of the manufacture and use of the compositions and methods of the invention. Since many embodiments of the invention can be made without departing from the spirit and scope of the invention, the invention resides in the claims hereinafter appended.

We claim:

1. A photoinitiator system for a cationically polymerizable resin, the photoinitiator system comprising:
   (a) an iodonium salt;
   (b) a visible light sensitizer; and
   (c) an electron donor compound having an oxidation potential greater than 0 and less than that of 1,4-dimethoxybenzene when measured versus a saturated calomel electrode, wherein the electron donor compound is selected from the group consisting of polycyclic aromatic compound and N-alkyl carbazole compounds;
   wherein the photoinitiator system has a photoinduced potential less than that of 3-dimethylaminobenzoic acid in a standard solution of $2.9 \times 10^{-5}$ moles/g diphenyl iodonium hexafluoroantimonate and $1.5 \times 10^{-5}$ moles/g camphorquinone in 2-butanone.

2. A photopolymerizable composition comprising:
   (a) a cationically polymerizable resin; and
   (b) a photoinitiator system for the cationically polymerizable resin, the photoinitiator system comprising:
      (i) an iodonium salt;
      (ii) a visible light sensitizer; and
      (iii) an electron donor compound having an oxidation potential greater than 0 and less than that of 1,4-dimethoxybenzene when measured versus a saturated calomel electrode, wherein the electron donor compound has a $pk_b$ greater than 8; and
   wherein the photoinitiator system has a photoinduced potential less than that of 3-dimethylaminobenzoic acid in a standard solution of $2.9 \times 10^{-5}$ moles/g diphenyl iodonium hexafluoroantimonate and $1.5 \times 10^{-5}$ moles/g camphorquinone in 2-butanone.

3. A photopolymerizable composition according to claim 2 wherein the cationically polymerizable resin is selected from the group consisting of epoxy, oxetane, vinyl ether and spiro-orthocarbonate resins, and combinations thereof.

4. A photopolymerizable composition according to claim 3 wherein the cationically polymerizable resin comprises an epoxy resin.

5. A photopolymerizable composition according to claim 4 wherein the cationically polymerizable resin comprises a silicon-containing epoxy resin.

6. A photopolymerizable composition according to claim 3 wherein the cationically polymerizable resin comprises a blend of a silicon-containing epoxy resin and an epoxy resin that does not contain silicon.

7. A photopolymerizable composition according to claim 2 wherein the iodonium salt is selected from the group consisting of diaryliodonium hexafluorophosphate, diaryliodonium hexafluoroantimonate, 4-octyloxyphenyl phenyliodonium hexafluoroantimonate, 4-(2-hydroxytetradylecoxyphenyl) phenyliodonium hexafluoroantimonate, 4-(1-methylethyl)phenyl 4-methylphenyliodonium tetrakis(pentafluorophenyl)borate, and combinations thereof.

8. A photopolymerizable composition according to claim 2 wherein the visible light sensitizer is selected from the group consisting of ketones, coumarin dyes, xanthene dyes, fluorone dyes, fluorescein dyes, aminoketone dyes, p-substituted aminostyryl ketone compounds, and combinations thereof.

9. A photopolymerizable composition according to claim 2 wherein the visible light sensitizer is an alpha-diketone.

10. A photopolymerizable composition according to claim 2 wherein the electron donor compound increases the polymerization speed of the photopolymerizable composition relative to the same composition but not containing an electron donor compound.

11. A photopolymerizable composition according to claim 2 wherein the electron donor compound is soluble in the photopolymerizable composition.

12. A photopolymerizable composition according to claim 2 wherein the electron donor compound does not absorb a significant amount of light at the wavelength of the light used to photopolymerize the composition.

13. A photopolymerizable composition according to claim 2 wherein the electron donor compound is substantially non-light absorbing at the wavelength at which the visible light sensitizer displays maximum light absorption.

14. A photopolymerizable composition according to claim 2 wherein the composition cures after less than about 2 minutes exposure to a light source that generates light of a wavelength to which the visible light sensitizer is sensitive.

15. A photopolymerizable composition according to claim 2 wherein the electron donor compound has an oxidation potential less than about 1.35 volts when measured using a saturated calomel electrode.

16. A photopolymerizable composition according to claim 15 wherein the electron donor compound has an oxidation potential between about 0.5 and 1.34 volts when measured using a saturated calomel electrode.

17. A photopolymerizable composition comprising:
   (a) a cationically polymerizable resin; and
   (b) a photoinitiator system for the cationically polymerizable resin, the photoinitiator system comprising:
      (i) an iodonium salt;
      (ii) a visible light sensitizer; and
      (iii) an electron donor compound having an oxidation potential greater than 0 and less than that of 1,4- dimethoxybenzene when measured versus a saturated calomel electrode, wherein the electron donor compound is selected from the group consisting of polycyclic aromatic compounds and N-alkyl carbazole compounds; and wherein the photoinitiator system has a photoinduced potential less than that of 3-dimethylaminobenzoic acid in a standard solution of $2.9\times10^{-5}$ moles/g diphenyl iodonium hexafluoroantimonate and $1.5\times10^{-5}$ moles/g camphorquinone in 2-butanone.

18. A photopolymerizable composition according to claim 17 wherein the polycyclic aromatic electron donor compound is selected from the group consisting of biphenylenes, naphthalenes, anthracenes, benzanthracenes, pyrenes, azulenes, pentacenes, decacyclenes, and derivatives and combinations thereof.

19. A photopolymerizable composition comprising:

(a) a cationically polymerizable resin; and (b) a photoinitiator system for the cationically polymerizable resin, the photoinitiator system comprising:

(i) an iodonium salt;

(iii) a visible light sensitizer; and (iii) an electron donor compound having an oxidation potential greater than 0 and less than that of 1,4-dimethoxybenzene when measured versus a saturated calomel electrode; wherein the electron donor compound is a polycyclic aromatic compound having one of the following structures:

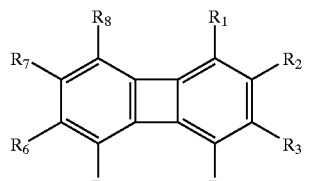

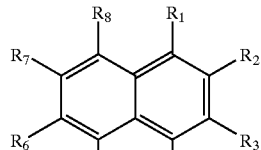

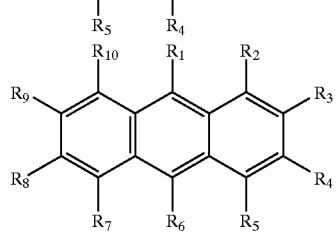

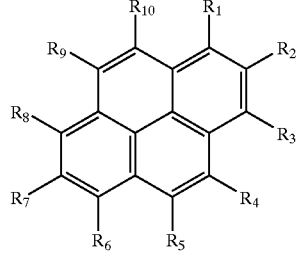

-continued

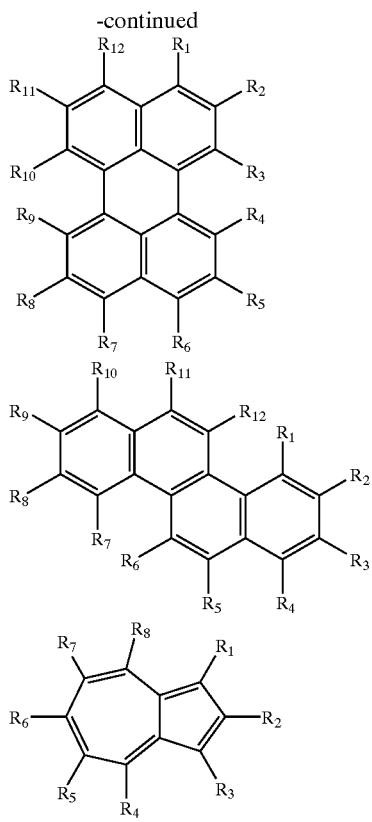

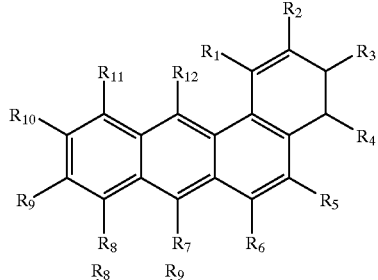

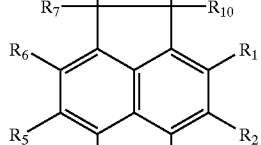

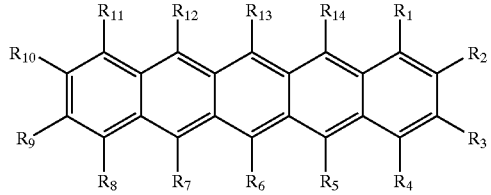

wherein each of $R_1$ to $R_{14}$ is independently selected from H, or alkyl or aromatic hydrocarbon groups, wherein the alkyl or aromatic hydrocarbon groups may be optionally substituted by one or more halogen, —CN, —OH, —SH, —COON, —COOC$_{1-10}$ alkyl, —(C$_{1-10}$ alkyl)$_{0-1}$—COH$_2$—(C$_{1-10}$ alkyl)$_{0-1}$—CO—C$_{1-10}$alkyl, or —CO—C—C$_{1-10}$ alkyl groups, and further wherein any of $R_1$ to $R_{14}$ may cooperate to form an aromatic or cycloalkyl ring; and wherein the photoinitiator system has a photoinduced potential less than that of 3-dimethylaminobenzoic acid in a standard solution of $2.9 \times 10^{-5}$ moles/g diphenyl iodonium hexafluoroantimonate and $1.5 \times 10^{-5}$ moles/g camphorquinone in 2-butanone.

20. A photopolymerizable composition comprising:
(a) a cationically polymerizable resin; and
(b) a photoinitiator system for the cationically polymerizable resin, the photoinitiator system comprising:
  (i) an iodonium salt;
  (ii) a visible light sensitizer; and
  (iii) an electron donor compound having an oxidation potential greater than 0 and less than that of 1,4-dimethoxybenzene when measured versus a saturated calomel electrode, wherein the electron donor compound is an N-alkyl carbazole compound having the following structure:

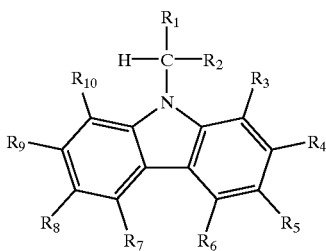

wherein each $R_1$ to $R_{10}$ is independently selected from H, or alkyl or aromatic hydrocarbon groups, wherein the alkyl and aromatic hydrocarbon groups may be optionally substituted by one or more halogen, —CN, —OH, —SH, —COOH, —COOC$_{1-10}$ alkyl, —(C$_{1-10}$ alkyl)$_{0-1}$—COH, —(C$_{1-10}$ alkyl)$_{0-1}$—CO—C$_{1-10}$ alkyl, —CO—C$_{1-10}$ alkyl, and further wherein $R_1$ and $R_{10}$ may cooperate to form an aromatic, cycloalkyl or low basicity heterocyclic ring; and
  wherein the photoinitiator system has a photoinduced potential less than that of 3-dimethylaminobenzoic acid in a standard solution of $2.9 \times 10^{-5}$ moles/g diphenyl iodonium hexafluoroantimonate and $1.5 \times 10^{-5}$ moles/g camphorquinone in 2-butanone.

21. A photopolymerizable composition according to claim 2 further comprising a free-radically polymerizable resin.

22. A photopolymerizable composition according to claim 2 further comprising a hydroxyl-containing material.

23. A photopolymerizable composition according to claim 2 wherein the photopolymerizable composition is a photopolymerizable adhesive.

24. A photopolymerizable composition comprising:
(a) a cationically polymerizable resin; and
(b) a photoinitiator system for the cationically polymerizable resin, the photoinitiator system comprising:
  (i) an iodonium salt;
  (ii) a visible light sensitizer; and
  (iii) an electron donor compound having an oxidation potential greater then 0 and less than that of 1,4-dimethoxybenzene when measured versus a saturated calomel electrode, wherein the photopolymerizable composition is a curable ink imaging layer, a silverless imaging layer, an imaging layer on a projection plate, or an imaging layer on a laser plate; and
wherein tho photoinitiator system has a photoinduced potential less than that of 3-dimethylaminobenzoic acid in a standard solution of $2.9 \times 10^{-5}$ moles/g diphenyl iodonium hexafluoroantimonate and $1.5 \times 10^{-5}$ moles/g camphorquinone in 2-butanone.

25. A photopolymerizable composition comprising:
(a) a cationically polymerizable resin; and
(b) a photoinitiator system for the cationically polymerizable resin, the photoinitiator system comprising:
  (i) an iodonium salt;
  (ii) a visible light sensitizer; and
  (iii) an electron donor compound having an oxidation potential greater than 0 and less than that of 1,4-dimethoxybenzene when measured versus a saturated calomel electrode, wherein the photopolymerizable composition has been polymerized to provide a hard coat layer on an optical lens; and
wherein the photoinitiator system has a photoinduced potential less than that of 3-dimethylaminobenzoic acid in a standard solution of $2.9 \times 10^{-5}$ moles/g diphenyl iodonium hexafluoroantimonate and $1.5 \times 10^{-5}$ moles/g camphorquinone in 2-butanone.

26. A photopolymerizable composition comprising:
(a) a cationically polymerizable resin; and
(b) a photoinitiator system for the cationically polymerizable resin, the photoinitiator system comprising:
  (i) an iodonium salt;
  (ii) a visible light sensitizer; and
  (iii) an electron donor compound having an oxidation potential greater than 0 and less than that of 1,4-dimethoxybenzene when measured versus a saturated calomel electrode, wherein the photopolymerizable composition has been polymerized to provide a coating on an optical fiber; and
wherein the photoinitiator system has a photoinduced potential less than that of 3-dimethylaminobenzoic acid in a standard solution of $2.9 \times 10^{-5}$ moles/g diphenyl iodonium hexafluoroantimonate and $1.5 \times 10^{-5}$ moles/g camphorquinone in 2-butanone.

27. A photopolymerizable dental material comprising:
(a) an epoxy resin; and
(b) a photoinitiator system for the epoxy resin, the photoinitiator system comprising:
  (i) an iodonium salt;
  (ii) a visible light sensitizer; and
  (iii) a polycyclic aromatic electron donor compound having an oxidation potential greater than 0 and less than that of 1,4-dimethoxybenzene when measured versus a saturated calomel electrode; and
  wherein the photoinitiator system has a photoinduced potential less than that of 3-dimethylaminobenzoic acid in a standard solution of $2.9 \times 10^{-5}$ moles/g diphenyl iodonium hexafluoroantimonate and $1.5 \times 10^{-5}$ moles/g camphorquinone in 2-butanone.

28. A photopolymerizable dental material according to claim 27 wherein the epoxy resin is a silicon-containing epoxy resin.

29. A photopolymerizable dental material according to claim 27 wherein the epoxy resin comprises a blend of a silicon-containing epoxy resin and an epoxy resin that does not contain silicon.

30. A photopolymerizable dental material according to claim 27 wherein the polycyclic aromatic electron donor compound is selected from the group consisting of biphenylenes, naphthalenes, anthracenes, benzanthracenes, pyrenes, cadence, pentacenes, decacyclenes, and derivatives and combinations thereof.

31. A photopolymerizable dental material according to claim 30 wherein the visible light sensitizer is selected from the group consisting of ketones, coumarin dyes, xanthene dyes, fluorone dyes, and fluorescein dyes, and combinations thereof.

32. A photopolymerizable dental material according to claim 31 wherein the iodonium salt is selected from the group consisting of diaryliodonium hexafluorophosphate, diaryliodonium hexafluoroantimonate, 4-octyloxyphenyl phenyliodonium hexafluoroantimonate, 4-(2-hydroxytetradecyloxyphenyl) phenyliodonium hexafluoroantimonate, 4(1-methylethyl)phenyl 4-methylphenyliodonium tetrakis(pentafluorophenyl)borate, and combinations thereof.

33. A photopolymerizable dental material according to claim 27 wherein the photopolymerizable dental material further comprises a free-radically polymerizable resin.

34. A photopolymerizable dental material according to claim 27 wherein the photopolymerizable dental material further comprises a hydroxyl-containing material.

35. A photopolymerizable dental material comprising:
(a) an epoxy resin; and
(b) a photoinitiator system for the epoxy resin, the photoinitiator system comprising:
  (i) an iodonium salt;
  (ii) a visible light sensitizer; and
  (iii) an N-alkyl carbazole electron donor compound having an oxidation potential greater than 0 and less than that of 1,4-dimethoxybenzene when measured versus a saturated calomel electrode; and
wherein the photoinitiator system has a photoinduced potential less than that of 3-dimethylaminobenzoic acid in a standard solution of $2.9 \times 10^{-5}$ moles/g diphenyl iodonium hexafluoroantimonate and $1.5 \times 10^{-5}$ moles/g camphorquinone in 2-butanone.

36. A photopolymerizable dental material according to claim 35 wherein the epoxy resin is a silicon-containing epoxy resin.

37. A photopolymerizable dental material according to claim 35 wherein the epoxy resin comprises a blend of a silicon-containing epoxy resin and an epoxy resin that does not contain silicon.

38. A photopolymerizable dental material according to claim 35 wherein the N-alkyl carbazole electron donor compound is N-methyl carbazole.

39. A photopolymerizable dental material according to claim 38 wherein the visible light sensitizer is selected from the group consisting of ketones, coumarin dyes, xanthene dyes, fluorone dyes, and fluorescein dyes, and combinations thereof.

40. A photopolymerizable dental material according to claim 39 wherein the iodonium salt is selected from the group consisting of diaryliodonium hexafluorophosphate, diaryliodonium hexafluoroantimonate, 4-octyloxyphenyl phenyliodonium hexafluoroantimonate, 4-(2-hydroxytetradecyloxyphenyl) phenyliodonium hexafluoroantimonate, 4-(1-methylethyl)phenyl 4-methylphenyliodonium tetrakis(pentafluorophenyl)borate, and combinations thereof.

41. A photopolymerizable dental material comprising:
(a) an epoxy resin; and
(b) a photoinitiator system for the epoxy resin, the photoinitiator system comprising:
  (i) an iodonium salt selected from the group consisting of diaryliodonium hexafluorophosphate, diaryliodonium hexafluoroantimonate, 4-octyloxyphenyl phenyliodonium hexafluoroantimonate, 4-(2-hydroxytetradecyloxyphenyl) phenyliodonium hexafluoroantimonate; 4-(1-methylethyl)phenyl 4-methylphenyliodonium tetrakis(pentafluorophenyl)borate, and combinations thereof;
  (ii) an alpha-diketone visible light sensitizer; and
  (iii) an electron donor compound selected from the group consisting of biphenylene, anthracene, 9-methylanthracene, 9-vinyl anthracene, 9-phenylanthracene, 9,10-diphenylanthracene, 9,10-dimethylanthracene, 2-ethylanthracene, acenaphthene, pyrene, pentacene, decacyclene, azulene, 7,12-dimethyl-1,2-benzanthracene, 1,2-benzanthracene, 1,4-dimethylnaphthalene, 2,3,5-trimethylnaphthalene, N-methyl carbazole, and combinations thereof;
wherein the photoinitiator system has a photoinduced potential less than that of 3-dimethylaminobenzoic acid in a standard solution of $2.9 \times 10^{-5}$ moles/g diphenyl iodonium hexafluoroantimonate and $1.5 \times 10^{-5}$ moles/g camphorquinone in 2-butanone.

42. A photopolymerizable dental material according to claim 41 wherein the alpha-diketone visible light sensitizer is camphorquinone.

43. A photopolymerizable dental material according to claim 42 wherein the dental material is a dental adhesive or a dental composite.

44. A method of reducing the time needed to polymerize a cationically polymerizable resin, the method comprising the steps of:
(a) providing a cationically polymerizable resin;
(b) providing a photoinitiator system for the cationically polymerizable resin, the photoinitiator system comprising:
  (i) an iodonium salt;
  (ii) a visible light sensitizer; and
  (iii) an electron donor compound having an oxidation potential greater than 0 and less tan that of 1,4-dimethoxybenzene when measured versus a saturated calomel electrode, wherein the electron donor compound has a $pk_b$ greater than 8; and
wherein the photoinitiator system has a photoinduced potential less than that of 3-dimethylaminobenzoic acid in a standard solution of $2.9 \times 10^{-5}$ moles/g diphenyl iodonium hexafluoroantimonate and $1.5 \times 10^{-5}$ moles/g camphorquinone in 2-butanone;
(c) combining the cationically polymerizable resin and the photoinitiator system to provide a polymerizable mixture; and
(d) exposing the polymerizable mixture to a light source having a wavelength and intensity to which the photoinitiator system is reactive and for a time until the polymerizable mixture attains a hard, tack-free state;
wherein the time until the polymerizable mixture attains a hard, tack-free state is less than the time required for the same polymerizable mixture, but excluding the electron donor compound, to achieve the same hard, tack-free state when exposed to the same light source.

* * * * *

UNITED STATES PATENT AND TRADEMARK OFFICE
CERTIFICATE OF CORRECTION

PATENT NO. : 6,765,036 B2
DATED : July 20, 2004
INVENTOR(S) : Dede, Karsten

It is certified that error appears in the above-identified patent and that said Letters Patent is hereby corrected as shown below:

Title page,
Item [56], References Cited, OTHER PUBLICATIONS, "Beringer et al.," reference, delete "Slats" and insert -- Salts --, therefor.

Column 12,
Line 1, delete "3-bomanedione" and insert -- 3-bornanedione --.

Column 15,
Line 28, after "alkyl," insert -- CO-C1-10 alkyl, --.

Column 16,
Line 1, after "alkyl," insert -- CO-$C_{1-10}$ alkyl, --.
Line 6, delete "nitrites" and insert -- nitriles --, therefor.

Column 18,
Line 59, delete "VIU" and insert -- VIII --, therefor.

Column 20,
Line 61, delete "chloromethane" and insert -- dichloromethane --, therefor.

Column 25,
Line 44, delete "compound" and insert -- compounds --, therefor.

Column 27,
Line 31, delete ";" and insert -- , --, therefor.

Column 28,
Line 63, delete "-COON" and insert -- -COOH --, therefor.
Lines 63-64, delete "-$(C_{1-10}$ alkyl$)_{0-1}$-$COH_2$" and insert -- $(C_{1-10}$ alkyl$)_{0-1}$-COH, -- therefor.
Line 65, delete "-CO-C-$C_{1-10}$" and insert -- -CO-$C_{1-10}$ --, therefor.

Column 29,
Line 56, delete "then" and insert -- than --, therefor.
Line 63, delete "tho" and insert -- the --, therefor.

UNITED STATES PATENT AND TRADEMARK OFFICE
CERTIFICATE OF CORRECTION

PATENT NO. : 6,765,036 B2
DATED : July 20, 2004
INVENTOR(S) : Dede, Karsten

It is certified that error appears in the above-identified patent and that said Letters Patent is hereby corrected as shown below:

Column 30,
Line 8, delete "1.4-" and insert -- 1,4- --, therefor.
Line 61, delete "cadence" and insert -- azulenes --, therefor.

Column 31,
Line 7, delete "4 (1-methylethyl)phenyl" and insert -- 4-(1-methylethyl)phenyl, -- therefor.
Line 30, delete "1.5X10-" and insert -- 1.5X10-5 --, therefor.

Column 32,
Line 3, delete ";" and insert -- , --, therefor.

Signed and Sealed this

Twenty-third Day of November, 2004

JON W. DUDAS
*Director of the United States Patent and Trademark Office*